US009511010B2

(12) United States Patent
Van Den Nest et al.

(10) Patent No.: US 9,511,010 B2
(45) Date of Patent: Dec. 6, 2016

(54) COMPOUNDS USEFUL IN THE TREATMENT AND/OR CARE OF THE SKIN, HAIR AND/OR MUCOUS MEMBRANES AND THEIR COSMETIC OR PHARMACEUTICAL COMPOSITIONS

(71) Applicant: Lubrizol Advanced Materials, Inc., Cleveland, OH (US)

(72) Inventors: Wim Van Den Nest, Vilanova i la Geltru (ES); Cristina Carreño Serraïma, Barcelona (ES); Raquel Delgado González, Gavá-Barcelona (ES); Antonio Vicente Ferrer Montiel, Alicante (ES)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 14/649,747

(22) PCT Filed: Dec. 3, 2013

(86) PCT No.: PCT/EP2013/075401
§ 371 (c)(1),
(2) Date: Jun. 4, 2015

(87) PCT Pub. No.: WO2014/086785
PCT Pub. Date: Jun. 12, 2014

(65) Prior Publication Data
US 2015/0342852 A1 Dec. 3, 2015

(30) Foreign Application Priority Data

Dec. 5, 2012 (EP) .................................... 12382484

(51) Int. Cl.
| | | |
|---|---|---|
| *A61K 38/00* | (2006.01) | |
| *A61K 38/08* | (2006.01) | |
| *A61K 38/10* | (2006.01) | |
| *A61K 8/64* | (2006.01) | |
| *A61Q 19/08* | (2006.01) | |
| *A61Q 5/00* | (2006.01) | |
| *C07K 7/06* | (2006.01) | |
| *C07K 7/08* | (2006.01) | |

(52) U.S. Cl.
CPC ............... *A61K 8/64* (2013.01); *A61K 38/08* (2013.01); *A61Q 5/002* (2013.01); *A61Q 19/08* (2013.01); *C07K 7/06* (2013.01); *A61K 38/00* (2013.01); *A61K 2800/59* (2013.01); *A61K 2800/74* (2013.01)

(58) Field of Classification Search
CPC  A61K 2800/59; A61K 2800/74; A61K 38/00; A61K 38/08; A61K 38/10; A61K 8/64; A61Q 19/08; A61Q 5/002; C07K 7/06; C07K 7/08
USPC ......... 424/59; 514/18.8, 21.8; 530/329, 325, 530/326, 327, 328
See application file for complete search history.

(56) References Cited

U.S. PATENT DOCUMENTS

2006/0198800 A1* 9/2006 Dilallo ................. A61K 8/0212
424/59
2009/0104177 A1* 4/2009 Klussmann ............ C07K 14/47
424/130.1

FOREIGN PATENT DOCUMENTS

WO    WO 2004/101607    * 11/2004    ............... C07K 7/00

OTHER PUBLICATIONS

Tran, et al. "DNA repair pathway stimulated by the forkhead transcription factor FOXO3a through the Gadd45 protein", Science, vol. 296, pp. 530-534 (2002).
Kirkwood, et al., "Why do we age?," Nature, vol. 408, pp. 233-238 (2000).
Wong, Journal of Experimental & Clinical Cancer Research, vol. 30, pp. 1-14 (2011).
Khanna, et al., "Ionizing radiation and UV induction of p53 protein by different pathways in ataxia-telangiectasia cells", Oncogene, vol. 8, pp. 3307-3312 (1993).
Le-Niculescu, et al. "Withdrawal of survival factors results in activation of the JNK pathway in neuronal cells leading to Fas ligand induction and cell death", Mol. Cell. Biol., vol. 19, pp. 751-763 (1999).
Zhou, et al., "The DNA damage response: putting checkpoints in perspective", Nature, vol. 408, pp. 433-439 (2000).
Calnan, et al., "The FoxO code", Oncogene, vol. 27, pp. 2276-2288 (2008).
Ogg, et al. "The Fork head transcription factor DAF-16 transduces insulin-like metabolic and longevity signals in C. Elegans", Nature, vol. 389, pp. 994-999 (1997).
Larsen, "Aging and resistance to oxidative damage in Caenorhabditis elegans" Proc Natl Acad Sci USA, vol. 90, pp. 8905-8909 (1993).
Brunet, et al. "Akt promotes cell survival by phosphorylating and inhibiting a Forkhead transcription factor", Cell, vol. 96, pp. 857-868 (1999).
Murphy, "The search for DAF-16/FOXO transcriptional targets: Approaches and discoveries", Exp Gerontol., vol. 41(10), pp. 910-921(2006).
Dorman, et al. "The age-1 and daf-2 genes function in a common pathway to control the lifespan of C elegans", Genetics, vol. 141, pp. 1399-1406 (1995).
Clancy, et al. "Extension of Life-Span by Loss of CHICO a Drosophila Insulin Receptor Substrate Protein", Science, vol. 292, pp. 104-106 (2001).

(Continued)

*Primary Examiner* — Julie Ha
(74) *Attorney, Agent, or Firm* — Fay Sharpe LLP

(57) ABSTRACT

Compounds of general formula (I):

$$R_1\text{-}W_n\text{-}X_m\text{-}AA_1\text{-}AA_2\text{-}AA_3\text{-}AA_4\text{-}AA_5\text{-}AA_6\text{-}Y_p\text{-}Z_q\text{-}R_2 \quad (I)$$

their stereoisomers, mixtures thereof and/or their cosmetically or pharmaceutically acceptable salts, cosmetic and/or pharmaceutical compositions which contain them and their use in medicine, and in processes of treatment and/or care of the skin, hair and/or mucous membranes, in particular in the aging and photoaging of the skin, are described.

21 Claims, No Drawings

(56) References Cited

OTHER PUBLICATIONS

Holzenberger, et al. "IGF-1 receptor regulates lifespan and resistance to oxidative stress in mice", Nature, vol. 421(6919), pp. 182-187 (2003).
Kim, et al. "Downregulation of Foxo3a accelerates cellular senescence in HDFs", J. Geront. A Bio. Sci. Med. Sci., vol. 60, pp. 4-9 (2005).
Ji-Hye Paik, et al. "FoxOs are lineage-restricted redundant tumor suppressors and critical regulators of endothelial cell homeostasis", Cell, vol. 128(2), pp. 309-323 (2007).
Lin, et al. "Unregulated miR-96 Induces Cell Proliferation in Human Breast Cancer by Downregulating Transcriptional Factor FOXO3a", PLoS ONE, vol. 5(12), e15797, pp. 1-10 (2010).
IUPAC-IUB Commission of Biochemical Nomenclature specified in Eur. J. Biochem., vol. 138, pp. 9-37(1984).
Roberts, et al., "Unusual amino acids in peptide synthesis," The Peptides, vol. 5, Chapter VI, Gross and Meienhofer J., Eds., Academic Press, New York, pp. 341-449 (1983).
Berge, et al., "Pharmaceutical Salts", J. Pharm. Sci., vol. 66, pp. 1-19 (1977).
Stewart, et al., "Solid-phase Peptide Synthesis," $2^{nd}$ Edition, pp. 1-20 (1984).
Bodanzsky, et al., "The practice of Peptide Synthesis," pp. 75-126 (1994).
Llyod-Williams, et al., "Chemical Approaches to the Synthesis of Peptides and Proteins," CRC, Synthesis in solution, Enzymatic synthesis, pp. 19-93 (1997).
Kullmann, "Proteases as catalysts for enzymic syntheses of opioid peptides", J.Biol.Chem., vol. 255(17), pp. 8234-8238 (1980).
Lloyd-Williams, et al., "Convergent Solid-Phase Peptide Synthesis", Tetrahedron, vol. 49(48), pp. 11065-11133 (1993).
Atherton, E., et al., "Solid Phase Peptide Synthesis: A practical approach," IRL Oxford University Press. pp. 1-61 (1989).
Matsueda, et al., "A p-methylbenzhydrylamine resin for improved solid-phase synthesis of peptide amides", Peptides, vol. 2, pp. 45-50 (1981).

Barlos, et al., "Darstellung geschützter Peptid-Fragmente unter Einsatz substituierter Triphenylmethyl-Harze", Tetrahedron Lett., vol. 30, pp. 3943-3946 (1989). (English Abstract only).
Barlos, et al., "Veresterung von partiell geschützten Peptid-Fragmenten mit Harzen. Einsatz von 2-Chlorotritylchlorid zur Synthese von Leu1-Gastrin I", Tetrahedron Lett., vol. 30, pp. 3947-3951(1989). (English Abstract Only).
Albericio, et al., "Preparation and application of the 5-(4-(9-fluorenylmethyloxycarbonyl) aminomethyl-3,5-dimethoxyphenoxy)valeric acid (PAL) handle for the solid-phase synthesis of C-terminal peptide amides under mild conditions", J. Org. Chem., 55, pp. 3730-3743 (1990).
Rink, "Solid-phase synthesis of protected peptide fragments using a trialkoxy-diphenyl-methylester resin," Tetrahedron Lett., vol. 28, pp. 3787-3790 (1987).
Wang, "p-Alkoxybenzyl Alcohol Resin and p-Alkoxybenzyloxycarbonylhydrazide Resin for Solid Phase Synthesis of Protected Peptide Fragments", J.Am.Chem.Soc., vol. 95, pp. 1328-1333 (1973).
Wilkinson, et al., "Harry's Cosmeticology," Seventh Edition Longman House, Essex, G.B. pp. 50-73 and 757-799 (1982).
Schaab, "Application of microencapsulation in textiles", HAPPI, May 1986, pp. 55-62 (1986).
Hipler, et al., "Biofunctional Textiles and the Skin," Curr. Probl. Dermatol. V. 33, pp. 35-41(2006).
Malcolm, et al., "Controlled release of a model antibacterial drug from a novel self-lubricating silicone biomaterial",J. Cont. Release, vol. 97(2), pp. 313-320 (2004).
Gottschalck, et al., Eds., "CTFA International Cosmetic Ingredient Dictionary and Handbook," $12^{th}$ Edition, pp. 3040-3065 (2008).
Kaiser, et al., "Color test for detection of free terminal amino groups in the solid-phase synthesis of peptides," Anal. Biochem., vol. 34(2), pp. 595-598 (1970).
Christensen, "A Qualitative Test for Monitoring Coupling Completeness in Solid Phase Peptide Synthesis Using Chloranil," Acta Chem. Scand., 33B, pp. 763-766 (1979).
Nelson, "Application of microencapsulation in textiles," Int. J. Pharm., 242(1-2), pp. 55-62 (2002).

* cited by examiner

COMPOUNDS USEFUL IN THE TREATMENT AND/OR CARE OF THE SKIN, HAIR AND/OR MUCOUS MEMBRANES AND THEIR COSMETIC OR PHARMACEUTICAL COMPOSITIONS

This application claims the benefit of PCT/EP2013/075401, filed Dec. 3, 2013, and EP 12382484.9, filed Dec. 5, 2012, from which the PCT application claims priority, the disclosures of which are incorporated herein by reference in their entireties.

FIELD OF THE INVENTION

This invention relates to compounds capable of accelerating the DNA protection and repair process and cosmetic or pharmaceutical compositions which contain said compounds useful in the treatment and/or care of the skin, hair and/or mucous membranes, preferably for the treatment and/or care of those conditions, disorders and/or diseases which are a consequence of damage to DNA, in particular, those caused by environmental factors.

BACKGROUND OF THE INVENTION

Cell aging, particularly dermal cell aging, has been widely studied. One of the most important factors in cell aging is the formation and accumulation of free radicals inside the cells. As well as natural aging, several environmental factors such as pollutants or ultraviolet radiation are capable of damaging skin cells by increasing the quantity of reactive oxygen species (ROS), altering DNA stability and interfering in cell functions, thus causing cell and tissue aging, and increasing the risk of developing cancer.

When DNA damage is caused two different pathways can be activated depending on the level of alteration caused by this damage, i.e., cells can activate DNA repair pathways or programmed cell death pathways (apoptosis). This ability of the cells to repair the damage limited to DNA or inducing the controlled death of very damaged cells protects the tissues and increases the survival prospects of organisms [Tran H. et al. "*DNA repair pathway stimulated by the forkhead transcription factor FOXO3a through the Gadd45 protein*", *Science*, (2002), 296, 530-534; Kirkwood T B., Austad S N. "*Why do we age?*", *Nature*, (2000), 408, 233-238].

Apoptosis, or programmed cell death, is a common phenomenon in the development of multicellular mechanisms. Cells die as a response to a variety of stimuli and in the case of apoptosis the cell death occurs in a controlled and regulated way. This distinguishes apoptosis from other forms of necrosis where uncontrolled cell death results in cell lysis [Wong R., *Journal of Experimental & Clinical Cancer Research*, (2011), 30, 1-14]. In the case of apoptosis the cell actively participates in the process inducing its own suicide. According to some conditions, apoptosis depends on transcription and requires over expression of "death genes", such as p53 tumor suppressor [Khanna K K., Lavin M F., "*Ionizing radiation and UV induction of p53 protein by different pathways in ataxia-telangiectasia cells*", *Oncogene*, (1993), 8, 3307-3312], proapoptotic genes and some cytokines [Le-Niculescu H. et al. "*Withdrawal of survival factors results in activation of the JNK pathway in neuronal cells leading to Fas ligand induction and cell death*", *Mol. Cell. Biol.*, (1999), 19, 751-763]. However, if the level of DNA damage is not very high and the cells functions can be recovered, DNA repair processes will begin [Zhou B B., Elledge S J., "*The DNA damage response: putting checkpoints in perspective*", *Nature*, (2000), 408, 433-439].

One of the possible control strategies of DNA repair and cell apoptosis passes through FOXO ("forkhead transcription factors" subclass O) transcription factors. The family of FOXO transcription factors is a family of proteins which are very well conserved among all the species and it is involved in the maintenance of the integrity of the genome, playing an essential role in longevity and tumor suppression [Calnan D. R. and Brunet A., "*The FoxO code*", *Oncogene*, (2008), 27, 2276-2288]. There are four FOXO transcription factors in mammals, FOXO1, FOXO3, FOXO4 and FOXO6. The FOXO3a transcription factor induces the expression of a series of genes as key functions related to metabolism, tumor suppression, development and longevity. Specifically, FOXO3a induces the expression of genes which allow damaged DNA to be repaired (GADD45, DDB1), genes involved in the regulation of the cell cycle (p21, p27, cyclin G2), in apoptosis (BIM-1, bcl-6, Fas, Trail), in the protection of the cells against oxidative stress (MnSOD, catalase), in gluconeogenesis (PEPCK, Glucose-6-phosphatase), angiogenesis (Sprouty2) or in cell differentiation (Btg1), among others [Ogg S. et al. "*The Fork head transcription factor DAF-16 transduces insulin-like metabolic and longevity signals in C. Elegans*", *Nature*, (1997), 389, 994-999; Larsen P L., "*Aging and Resistance to Oxidative Damage in Caenorhabditis elegans*" *Proc Natl Acad Sci USA*, (1993), 90, 8905-8909; Tran H. et al. "*DNA Repair Pathway Stimulated by the Forkhead Protein Transcription Factor FOXO3a Through the Gadd45 Protein*", *Science*, (2002), 296, 530-534; Brunet A. et al. "*Akt promotes cell survival by phosphorylating and inhibiting a Forkhead transcription factor*", *Cell*, (1999), 96, 857-868; Murphy C. T., "*The search for DAF-16/FOXO transcriptional targets: Approaches and discoveries*", *Exp Gerontol.*, (2006), 41(10), 910-21].

One of the consequences of this genetic expression of FOXO3a is for example that FOXO3a is clearly linked to the longevity of human beings; it is described in the literature that activation of FOXO3a induces an increase in the lifespan of the worm *C elegans* [Dorman J. B. et al. "*The age-1 and daf-2 genes function in a common pathway to control the lifespan of C elegans*", (1995), *Genetics*, 141, 1399-1406], of the fruit fly [Clancy D. J. et al. "*Extension of Life-Span by Loss of CHICO a Drosophila Insulin Receptor Substrate Protein*", (2001), *Science*, 292, 104-106] or mice [Holzenberger M. et al. "*IGF-1 receptor regulates lifespan and resistance to oxidative stress in mice*", *Nature*, (2003), 421(6919), 182-187].

Furthermore, FOXO3a also plays a key role in delaying cell senescence and, therefore, aging [Kim H. K. et al. "*Downregulation of Foxo3a Accelerates cellular senescence in HDFs*", *J. Geront. A Bio. Sci. Med. Sci.*, (2005), 60, 4-9].

The relationship of FOXO transcription factors in the development of tumors is also widely described in scientific literature; and it has been demonstrated that an animal model in which the expression of all the FOXO proteins had been suppressed developed a cancerous condition characterized by the presence of abundant thymic lymphomas and hemangiomas [Ji-Hye Paik J. H et al. "*FoxOs are lineage-restricted redundant tumor suppressors and critical regulators of endothelial cell homeostasis*", *Cell*, (2007), 128(2), 309-323]. In the same way, inhibition of the expression of some of the FOXO transcription factors or of their activity can lead to the development of some types of cancer, such as breast cancer [Lin H. et al. "*Unregulated miR-96 Induces*

Cell Proliferation in Human Breast Cancer by Downregulating Transcriptional Factor FOXO3a", *PLoS ONE*, (2010), 5(12), e15797].

However, the quantity of FOXO which is active is not constant throughout the lifetime of human beings and with age the quantity of FOXO found in the inactive phosphorylated form increases [Kim H. K. et al. "*Downregulation of Foxo3a accelerates cellular senescence in HDFs*", J. Geront. *A Bio. Sci. Med. Sci.*, (2005), 60, 4-9]. It is for this reason that with age the natural abilities of the organism to repair DNA, regulate the cell cycle and protect the cells against oxidative stress are lost, and cell differentiation, aging and the appearance of tumors occurs.

Thus, there is the need to find compounds which stimulate the synthesis of proteins regulated by FOXO and which intervene in the aforementioned processes.

DESCRIPTION OF THE INVENTION

Definitions

In order to facilitate the comprehension of this invention, the meanings of some terms and expressions as they are used in the context of the invention are included.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes, mast cells, neurons and/or adipocytes among others. The term "skin" also comprises the scalp.

The term "treatment", according to its use in the context of this specification when it is not accompanied by the qualifications "cosmetic, non-therapeutic", means the administration of a compound according to the invention to alleviate or eliminate a disease or disorder or reduce or eliminate one or more symptoms associated with said disease or disorder. The term "treatment" also covers alleviating or eliminating physiological consequences of the disease or disorder.

When the term "treatment" is accompanied by the qualifications "cosmetic, non-therapeutic", it refers to the application of the compound to the skin, hair and/or mucous membranes in particular with the aim of improving the cosmetic qualities of the skin, hair and/or mucous membranes such as, for example and not restricted to, their level of hydration, elasticity, firmness, shine, tone or texture, among others. The term "care" in this invention refers to the maintenance of the qualities of the skin, hair and/or mucous membranes. Said qualities are subject to being improved or maintained by cosmetic treatment and/or care of the skin, hair and/or mucous membranes both in healthy subjects as well as in those which present diseases and/or disorders of the skin and/or mucous membranes such as, for example and not restricted to, ulcers and injuries to skin, psoriasis, dermatitis, acne or rosacea, among others.

The term "prevention", as used in this invention, refers to the ability of a compound of the invention to prevent, delay or hinder the appearance or development of a disease or disorder before its appearance or improve the cosmetic qualities of the skin, mucous membranes and/or hair.

In the context of this invention, the term "aging" refers to the changes experienced by the skin with age (chronoaging) or through exposure to the sun (photoaging) or to environmental agents such as tobacco smoke, extreme climatic conditions of cold or wind, chemical contaminants or pollutants, and includes all the external visible and/or perceptible changes through touch, such as and not restricted to, the development of discontinuities on the skin such as wrinkles, fine lines, expression lines, stretch marks, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and it presents the same physical characteristics as aging, such as and not restricted to, flaccidity, sagging, changes to the color or irregularities in the pigmentation, abnormal and/or excessive keratinization. The sum of various environmental factors such as exposure to tobacco smoke, exposure to pollution, and climatic conditions such as cold and/or wind also contribute to the aging of the skin.

In this invention "senescence" is understood to be the changes to the organism as it ages after maturity and which affect both the cells and their functions and the whole organism. "Cell senescence" is understood to be the loss of the cells for their replication capacity by themselves, resulting in a degradation of the cells over time. Cell senescence is particularly important in cells with the capacity to replicate in the central nervous system, such as astrocytes, endothelial cells and fibroblasts which play a key role in age-related diseases such as Alzheimer's disease, Parkinson's disease, Huntington's disease, and stroke; cells with finite replicative capacity in the integument, including fibroblasts, sebaceous gland cells, melanocytes, keratinocytes, Langerhans cells, and hair follicle cells which play a key role in age-related diseases in the integument, such as dermal atrophy, elastolysis, wrinkles, sebaceous gland hyperplasia, senile lentigo, graying and hair loss, chronic skin ulcers, and age-related deterioration of the wound healing capacity; cells with finite replicative capacity in joint cartilage, such as chondroctyes and synovial fibroblasts which play a key role in degenerative joint diseases; cells with finite replicative capacity in the bone, such as osteoblasts, bone marrow stromal fibroblasts and osteoprogenitor cells which play a key role in osteoporosis; cells with finite replicative capacity in the immune system such as B and T lymphocytes, monocytes, neutrophils, eosinophils, basophils, NK cells and their respective progenitors, which can play a key role in the age-related deterioration of the immune system; cells with finite replicative capacity in the vascular system, including endothelial cells, smooth muscle cells, and adventitial fibroblasts which can play a key role in age-related diseases of the vascular system including atherosclerosis, calcification, thrombosis, and aneurisms; and cells with finite replicative capacity in the eye, such as the pigmented epithelium and vascular endothelial cells which can play an important role in age-related macular degeneration.

In this description the abbreviations used for amino acids follow the rules of IUPAC-IUB Commission of Biochemical Nomenclature specified in *Eur. J. Biochem.*, (1984), 138, 9-37.

Thus, for example, Gly represents NH$_2$—CH$_2$—COOH, Gly- represents NH$_2$—CH$_2$—CO—, -Gly represents —NH—CH$_2$—COOH and -Gly- represents —NH—CH$_2$—CO—. Therefore, the hyphen, which represents the peptide bond, eliminates the OH in the 1-carboxyl group of the amino acid (represented here in the conventional non-ionized form) when situated to the right of the symbol, and eliminates the H of the 2-amino group of the amino acid when situated to the left of the symbol; both modifications can be applied to the same symbol (see Table 1).

TABLE 1

Structures of the amino acid residues and their nomenclature in one and three-letter code

| Name | Residue | Symbol | Residue |
|---|---|---|---|
| Asparaginyl -Asn- N | | Glutaminyl -Gln- Q | |
| Histidyl -His- H | | Glycyl -Gly- G | |
| Lysyl -Lys- K | | Tyrosyl -Tyr- Y | |
| Leucyl -Leu- L | | Prolyl -Pro- P | |
| Glutamyl -Glu- E | | Seryl -Ser- S | |
| Valyl -Val- V | | | |

The abbreviation "Ac-" is used in this description to designate the acetyl group (CH$_3$—CO—), the abbreviation "Palm-" is used to designate the palmitoyl group (CH$_3$—(CH$_2$)$_{14}$—CO—) and the abbreviation "Myr-" is used to designate the myristoyl group (CH$_3$—(CH$_2$)$_{12}$—CO—).

The term "non-cyclic aliphatic group" is used in this invention to cover the linear or branched alkyl, alkenyl and alkynyl groups.

The term "alkyl group" refers to a linear or branched saturated group, which has between 1 and 24, preferably between 1 and 16, more preferably between 1 and 14, even more preferably between 1 and 12, yet more preferably 1, 2, 3, 4, 5 or 6 carbon atoms and is bound to the rest of the molecule by a single bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more double carbon-carbon bonds, preferably with 1, 2 or 3 double carbon-carbon bonds, conjugated or unconjugated, which is bound to the rest of the molecule by a single bond, including, for example and not restricted to, the vinyl (—CH$_2$=CH$_2$), allyl (—CH$_2$—CH=CH$_2$), prenyl, oleyl, linoleyl groups and similar.

The term "alkynyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more triple carbon-carbon bonds, preferably 1, 2 or 3 triple carbon-carbon bonds, conjugated or unconjugated, which is bound to the rest of the molecule by a single bond, including, for example and not restricted to, the ethynyl group, 1-propynyl, 2-propynyl, 1-butynyl, 2-butynyl, 3-butynyl, pentynyl, such as 1-pentynyl, and similar. The alkynyl groups can also contain one or more double carbon-carbon bonds, including, for example and not restricted to, the but-1-en-3-ynyl, pent-4-en-1-ynyl groups and similar.

The term "alycyclic group" is used in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably 3, 4, 5 or 6 carbon atoms and which is bound to the rest of the molecule by a single bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more double carbon-carbon bonds, preferably 1, 2 or 3 double carbon-carbon bonds, conjugated or unconjugated, which is bound to the rest of the molecule by a single bond, including, for example and not restricted to, the cyclopent-1-en-1-yl group and similar.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more triple carbon-carbon bonds, preferably 1, 2 or 3 triple carbon-carbon bonds, conjugated or unconjugated, which is bound to the rest of the molecule by a single bond, including, for example and not restricted to, the cyclooct-2-yn-1-yl group and similar. Cycloalkynyl groups can also contain one or more double carbon-carbon bonds, including, for example and not restricted to, the cyclooct-4-en-2-ynyl group and similar.

The term "aryl group" refers to an aromatic group which has between 6 and 30, preferably between 6 and 18, more preferably between 6 and 10, yet more preferably 6 or 10 carbon atoms, which comprises 1, 2, 3 or 4 aromatic rings, bound by a carbon-carbon bond or fused, including, for example and not restricted to, phenyl, naphthyl, diphenyl, indenyl, phenanthryl or antranyl among others; or to an aralkyl group.

The term "aralkyl group" refers to an alkyl group substituted by an aromatic group, with between 7 and 24 carbon atoms and including, for example and not restricted to, $—(CH_2)_{1-6}$-phenyl, $—(CH_2)_{1-6}$-(1-naphthyl), $—(CH_2)_{1-6}$-(2-naphthyl), $—(CH_2)_{1-6}—CH(phenyl)_2$ and similar.

The term "heterocyclyl group" refers to a hydrocarbonated ring or system of rings of 3-10 members, in which one or more of the atoms in the ring or rings, preferably 1, 2 or 3 of the atoms of the ring or rings, is a different element to carbon, such as nitrogen, oxygen or sulfur and it can be saturated or unsaturated. For the purposes of this invention, the heterocycle can be a cyclic, monocyclic, bicyclic or tricyclic system, which may include systems of fused rings; and the nitrogen, carbon or sulfur atoms in the heterocyclyl radical may be optionally oxidized; the nitrogen atom may be optionally quaternized; and the heterocyclyl radical may be partially or completely saturated or be aromatic. The greatest preference is for the term heterocyclyl to refer to a ring of 5 or 6 members. Examples of saturated heterocyclyl groups are dioxane, piperidine, piperazine, pyrrolidine, morpholine and thiomorpholine. Examples of aromatic heterocyclyl groups, also known as heteroaromatic groups are pyridine, pyrrol, furan, thiophene, benzofuran, imidazoline, quinolein, quinoline, pyridazine and naphthyridine.

The term "heteroarylalkyl group" refers to an alkyl group substituted by a substituted or unsubstituted aromatic heterocyclyl group, the alkyl group having from 1 to 6 carbon atoms and the aromatic heterocyclyl group between 2 and 24 carbon atoms and from 1 to 3 atoms different to carbon including, for example and not restricted to, $—(CH_2)_{1-6}$-imidazolyl, $—(CH_2)_{1-6}$-triazolyl, $—(CH_2)_{1-6}$-thienyl, $—(CH_2)_{1-6}$-furyl, $—(CH_2)_{1-6}$-pyrrolidinyl and similar.

As is understood in this technical field, there may be a certain degree of substitution of the aforementioned groups. Therefore, there can be substitution in any of the groups of this invention where it is explicitly stated. The references in this document to substituted groups in the groups of this invention indicate that the specified radical can be substituted in one or more positions available by one or more substitutes, preferably in 1, 2 or 3 positions, more preferably in 1 or 2 positions, yet more preferably in 1 position. These substituents include, for example and not restricted to, alkyl $C_1$-$C_4$; hydroxyl; alcoxyl $C_1$-$C_4$; amino; aminoalkyl $C_1$-$C_4$; carbonyloxyl $C_1$-$C_4$; oxycarbonyl $C_1$-$C_4$; halogen such as fluoride, chlorine, bromine and iodine; cyano; nitro; azide; alkylsulfonyl $C_1$-$C_4$; thiol; alkylthio $C_1$-$C_4$; aryloxy such as phenoxyl; $—NR_b(C=NR_b)NR_bR_c$; wherein $R_b$ and $R_c$ are independently selected from the group formed by H, alkyl $C_1$-$C_4$, alkenyl $C_2$-$C_4$, alkynyl $C_2$-$C_4$, cycloalkyl $C_3$-$C_{10}$, aryl $C_6$-$C_{18}$, aralkyl $C_7$-$C_{17}$, heterocyclyl of 3-10 members or protective group of the amino group.

Compounds in the Invention

The applicant of the present invention has found a solution for the aforementioned problem of stimulation of the expression of proteins regulated by FOXO. A first aspect of the invention refers to a compound of general formula (I):

its stereoisomers, mixtures thereof and/or its cosmetically or pharmaceutically acceptable salts, where $AA_1$ is -Tyr-;
$AA_2$ is selected from the group formed by -Asn-, -His-, -Tyr- and -Glu-;
$AA_3$ is selected from the group formed by -Lys-, -Ser- and -Pro-;
$AA_4$ is selected from the group formed by -Gly-, -Leu-, -Lys- and -His-;
$AA_5$ is selected from the group formed by -Gln- and -Asn-;
$AA_6$ is -Val-;
W, X, Y, Z are amino acids and are independently selected from amongst themselves;
n, m, p and q are independently selected from amongst themselves and have a value of 0 or 1;
n+m+p+q is smaller or equal to 2;
$R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
$R_2$ is selected from the group formed by —$NR_3R_4$, —$OR_3$ and —$SR_3$, wherein $R_3$ and $R_4$ are independently selected from the group formed by H, a polymer derived from polyethylene glycol, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
$R_1$ or $R_2$ are not α-amino acids Groups $R_1$ and $R_2$ are bound to the amino-terminal (N-terminal) and carboxy-terminal (C-terminal) ends of the peptide sequences respectively.

In accordance with a preferred embodiment $R_1$ is selected from the group formed by H, a polymer derived from polyethylene glycol and $R_5$—CO—, wherein $R_5$ is selected from the group formed by substituted or unsubstituted alkyl radical $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon and an alkyl chain of 1 to 6 carbon atoms and $R_5$—CO— is not an α-amino acid. More preferably, $R_1$ is selected from the group formed by H, a polymer derived from polyethylene glycol with a molecular weight comprised between 200 and 35000 Daltons, acetyl, tert-butanoyl, prenyl, hexanoyl, 2-methylhexanoyl, cyclohexanecarboxyl, octanoyl, decanoyl, lauroyl myristoyl, palmitoyl, stearoyl, oleoyl and linoleoyl. Even more preferably, $R_1$ is H, acetyl, lauroyl, myristoyl or palmitoyl. In an even more preferred embodiment, $R_1$ is acetyl or palmitoyl.

In accordance with another preferred embodiment, $R_2$ is selected from the group formed by —$NR_3R_4$, —$OR_3$, —$SR_3$, wherein $R_3$ and $R_4$ are independently selected from the group formed by H, a polymer derived from polyethylene glycol, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms and —$NR_3R_4$ is not an α-amino acid. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$. More preferably, $R_3$ and $R_4$ are independently selected from the group formed by H, a polymer derived from polyethylene glycol with a molecular weight comprised between 200 and 35000 Daltons, methyl, ethyl, hexyl, dodecyl and hexadecyl. Even more preferably $R_3$ is H and $R_4$ is selected from the group formed by H, methyl, ethyl, hexyl, dodecyl and hexadecyl. In accordance with an even more preferred embodiment, $R_2$ is selected from —OH and —$NH_2$.

In accordance with another embodiment of this invention $R_1$ is selected from the group formed by H, acetyl, lauroyl, myristoyl and palmitoyl, preferably $R_1$ is selected from the group formed by H, acetyl and palmitoyl and $R_2$ is selected from the group formed by —OH and —$NH_2$.

In accordance with another particular embodiment the most preferred structures of the polymer derived from polyethylene glycol are the group (—$CH_2$—$CH_2$—O)$_r$—H in which r is a number comprised between 4 and 795 and the group

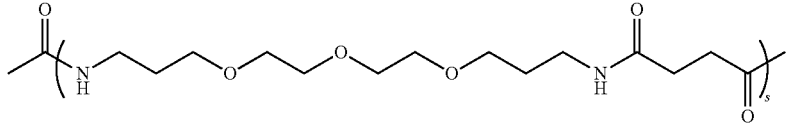

where s is a number comprised between 1 and 125.

In accordance with another embodiment of this invention n, m, p and q are 0.

In accordance with a preferred embodiment of this invention $AA_5$ is -Gln-. In accordance with a more preferred embodiment, $AA_2$ is selected from the group formed by -Asn-, -Glu- and -Tyr- and $AA_5$ is -Gln-. In accordance with an even more preferred embodiment, $AA_2$ is selected from the group formed by -Asn- and -Glu-, $AA_3$ is selected from the group formed by -Lys- and -Ser, $AA_4$ is selected from group formed by -Gly-, -Leu- and -Lys-, and $AA_5$ is -Gln-.

In accordance with another embodiment of this invention $R_1$ is selected from the group formed by H, acetyl, lauroyl, myristoyl and palmitoyl, is -L-Tyr-, $AA_2$ is -L-Asn-, $AA_3$ is -L-Lys-, $AA_4$ is -Gly-, $AA_5$ is -L-Gln-, $AA_6$ is -L-Val- and $R_2$ is selected from the group formed by —$NR_3R_4$ and —$OR_3$ wherein $R_3$ and $R_4$ are independently selected from H, methyl, ethyl, hexyl, dodecyl and hexadecyl. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl and palmitoyl, $AA_1$ is -L-Tyr-, $AA_2$ is -L-Glu-, $AA_3$ is -L-Lys-, $AA_4$ is -L-Leu-, $AA_5$ is -L-Gln-, $AA_6$ is -L-Val- and $R_2$ is selected from the group formed by —$NR_3R_4$ and —$OR_3$ wherein $R_3$ and $R_4$ are independently selected from H, methyl, ethyl, hexyl, dodecyl and hexadecyl. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl and palmitoyl, $AA_1$ is -L-Tyr-, $AA_2$ is -L-Glu-, $AA_3$ is -L-Ser-, $AA_4$ is -L-Lys-, $AA_5$ is -L-Gln-, $AA_6$ is -L-Val- and $R_2$ is selected from the group formed by —$NR_3R_4$ and —$OR_3$ wherein $R_3$ and $R_4$ are independently selected from H, methyl, ethyl, hexyl, dodecyl and hexadecyl. More preferably, $R_1$ is acetyl or palmitoyl and $R_2$ is —$NH_2$. Even more preferably, n, m, p and q are 0.

Specifically, the compounds of the invention which stimulate the expression of proteins regulated by FOXO, represented according to the formula (I) are selected from the group of sequences outlined in Table 2, in which their sequence identifier is detailed:

TABLE 2

| SEQUENCE | IDENTIFIER |
|---|---|
| Tyr-Asn-Lys-Gly-Gln-Val | SEQ ID NO: 1 |
| Tyr-Tyr-Ser-Leu-Asn-Val | SEQ ID NO: 2 |
| Tyr-Glu-Pro-Lys-Gln-Val | SEQ ID NO: 3 |
| Tyr-Asn-Lys-His-Gln-Val | SEQ ID NO: 4 |
| Tyr-Asn-Lys-Gly-Asn-Val | SEQ ID NO: 5 |
| Tyr-Tyr-Ser-Gly-Gln-Val | SEQ ID NO: 6 |

TABLE 2-continued

| SEQUENCE | IDENTIFIER |
|---|---|
| Tyr-Glu-Pro-Leu-Asn-Val | SEQ ID NO: 7 |
| Tyr-Asn-Lys-Lys-Gln-Val | SEQ ID NO: 8 |
| Tyr-Tyr-Ser-His-Asn-Val | SEQ ID NO: 9 |
| Tyr-Glu-Pro-Gly-Gln-Val | SEQ ID NO: 10 |
| Tyr-Asn-Lys-Leu-Asn-Val | SEQ ID NO: 11 |
| Tyr-Tyr-Ser-Lys-Gln-Val | SEQ ID NO: 12 |

TABLE 2-continued

| SEQUENCE | IDENTIFIER |
|---|---|
| Tyr-Glu-Pro-His-Asn-Val | SEQ ID NO: 13 |
| Tyr-Glu-Ser-Lys-Asn-Val | SEQ ID NO: 14 |
| Tyr-Tyr-Pro-Gly-Asn-Val | SEQ ID NO: 15 |
| Tyr-Glu-Ser-Gly-Gln-Val | SEQ ID NO: 16 |
| Tyr-Asn-Pro-Lys-Asn-Val | SEQ ID NO: 17 |
| Tyr-Asn-Pro-His-Gln-Val | SEQ ID NO: 18 |
| Tyr-Glu-Ser-His-Gln-Val | SEQ ID NO: 19 |
| Tyr-Tyr-Ser-His-Gln-Val | SEQ ID NO: 20 |
| Tyr-Asn-Lys-Leu-Gln-Val | SEQ ID NO: 21 |
| Tyr-Glu-Lys-Leu-Gln-Val | SEQ ID NO: 22 |
| Tyr-Tyr-Lys-Leu-Gln-Val | SEQ ID NO: 23 |
| Tyr-Glu-Ser-Lys-Gln-Val | SEQ ID NO: 24 |
| Tyr-His-Lys-Leu-Gln-Val | SEQ ID NO: 25 |
| Tyr-His-Ser-Lys-Gln-Val | SEQ ID NO: 26 |
| Tyr-Asn-Ser-Lys-Gln-Val | SEQ ID NO: 27 |
| Tyr-His-Pro-His-Gln-Val | SEQ ID NO: 28 |
| Tyr-Tyr-Pro-His-Gln-Val | SEQ ID NO: 29 |
| Tyr-His-Ser-His-Gln-Val | SEQ ID NO: 30 |
| Tyr-Asn-Lys-Leu-Gln-Val-Gly | SEQ ID NO: 31 |
| Tyr-Glu-Lys-Leu-Gln-Val-Ala | SEQ ID NO: 32 |
| Leu-Tyr-Tyr-Lys-Leu-Gln-Val | SEQ ID NO: 33 |
| Ala-Tyr-Glu-Ser-Lys-Gln-Val | SEQ ID NO: 34 |
| Gly-Leu-Tyr-Asn-Lys-Gly-Gln-Val | SEQ ID NO: 35 |
| Ala-Tyr-Asn-Pro-His-Gln-Val-Gly | SEQ ID NO: 36 |
| Asn-Glu-Tyr-Glu-Ser-His-Gln-Val | SEQ ID NO: 37 |
| Ala-Tyr-Tyr-Ser-His-Gln-Val-Leu | SEQ ID NO: 38 | their stereoisomers, mixtures thereof and/or their cosmetically or pharmaceutically acceptable salts.

The compounds of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomeric mixtures, or pure diastereomers or enantiomers, depending on the number of asymmetric carbons and on which isomers or isomeric mixtures are present. The preferred structures of the compounds of the invention are pure isomers, i.e., enantiomers or diastereomers.

For example, when it is stated that $AA_3$ can be -Lys-, it is understood that $AA_3$ is selected from -L-Lys-, -D-Lys- or mixtures of both, racemic or non-racemic. The preparation procedures described in this document enable the person skilled in the art to obtain each of the stereoisomers of the compound of the invention by choosing the amino acid with the right configuration.

In the context of this invention, the term "amino acids" includes the amino acids encoded by the genetic code as well as non-encoded amino acids, whether they are natural or not. Examples of non-encoded amino acids are, without restriction, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, β-alanine, norleucine, N-methyl amino acids, α-amino acids and β-amino acids, among others, as well as their derivatives. A list of non-natural amino acids can be found in the article "*Unusual amino acids in peptide synthesis*" by D. C. Roberts and F. Vellaccio, in *The Peptides*, Vol. 5 (1983), Chapter VI, Gross E. and Meienhofer J., Eds., Academic Press, New York, USA or in the commercial catalogues of the companies specialized in the field.

In the context of this invention, when n, m, p or q are not 0 it is clearly understood that the nature of W, X, Y and/or Z does not hinder the activity of the compounds of the invention, but it contributes to the stimulation of the expression of proteins regulated by FOXO or has no effect on it.

The cosmetically or pharmaceutically acceptable salts of the compounds provided within the present invention are also found within the field of this invention. The term "cosmetically or pharmaceutically acceptable salts" means a salt recognized for its use in animals and more specifically in human beings, and includes salts used to form base addition salts, either they are inorganic, for example and not restricted to, lithium, sodium, potassium, calcium, magnesium, manganese, copper, zinc or aluminum among others, or they are organic, for example and not restricted to, ethylamine, diethylamine, ethylenediamine, ethanolamine, diethanolamine, arginine, lysine, histidine or piperazine among others, or acid addition salts, either they are organic, for example and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, for example and not restricted to, chloride, sulfate, borate or carbonate, among others. The nature of the salt is not critical, provided that it is cosmetically or pharmaceutically acceptable. The cosmetically or pharmaceutically acceptable salts of the compounds of the invention can be obtained by the conventional methods, well known in the prior art [Berge S. M. et al., "*Pharmaceutical Salts*", (1977), *J. Pharm. Sci.*, 66, 1-19].

Preparation Procedures of the Compounds of the Invention

Synthesis of the compounds of the invention, their stereoisomers, mixtures thereof and/or their cosmetically or pharmaceutically acceptable salts can be carried out according to conventional methods, known in the prior art, such as using solid phase peptide synthesis methods [Stewart J. M. and Young J. D., "*Solid Phase Peptide Synthesis, 2nd Edition*", (1984), Pierce Chemical Company, Rockford, Ill.; Bodanzsky M. and Bodanzsky A., "*The practice of Peptide Synthesis*", (1994), Springer Verlag, Berlin; Lloyd-Williams P. et al., "*Chemical Approaches to the Synthesis of Peptides and Proteins*", (1997), CRC, Boca Raton, Fla., USA], synthesis in solution, enzymatic synthesis [Kullmann W. "*Proteases as catalysts for enzymic syntheses of opioid peptides*", (1980), *J. Biol. Chem.*, 255(17), 8234-8238] or any combination thereof. The compounds can also be obtained by fermentation of a bacterial strain, modified or unmodified, by genetic engineering with the objective of producing the desired sequences, or by controlled hydrolysis of proteins with animal or plant origins, preferably plant, which free peptide fragments that contain, at least, the desired sequence.

For example, a method of obtaining the compounds (I) of the invention, their stereoisomers and mixtures thereof comprises the stages of:
- coupling of an amino acid, with the N-terminal end protected and the C-terminal end free, with an amino acid with the N-terminal end free and the C-terminal end protected or bound to a solid support;
- elimination of the protective group of the N-terminal end;
- repetition of the coupling sequence and elimination of the protective group of the N-terminal end until the desired peptide sequence is obtained;
- elimination of the protective group of the C-terminal end or cleavage of the solid support.

Preferably, the C-terminal end is bound to a solid support and the process is carried out in solid phase and, therefore, comprises the coupling of an amino acid with the N-terminal end protected and the C-terminal end free with an amino acid with the N-terminal end free and the C-terminal end bound to a polymeric support; elimination of the protective group of the N-terminal end; and repetition of this sequence as many times as is necessary to thus obtain the compound of the desired length, finally followed by the cleavage of the synthesized compound from the original polymeric support.

The functional groups of the side chains of the amino acids are maintained conveniently protected with temporary or permanent protective groups throughout synthesis, and can be unprotected simultaneously or orthogonally to the process of cleavage of the peptide from the polymeric support.

Alternatively, solid phase synthesis can be carried out using a convergent strategy coupling a peptide with the polymeric support or with a peptide or an amino acid previously bound to the polymeric support. Convergent synthesis strategies are widely known by persons skilled in the art and are described in Lloyd-Williams P. et al., "Convergent Solid-Phase Peptide Synthesis", (1993), Tetrahedron, 49(48), 11065-11133.

The process can comprise the additional stages of deprotection of the N-terminal and C-terminal ends and/or cleavage of the peptide from the polymeric support in an indiscriminate order, using standard procedures and conditions known in the prior art, after which the functional groups of these ends can be modified. The optional modification of the N-terminal and C-terminal ends can be carried out with the peptide of formula (I) anchored to the polymeric support or once the peptide has been separated from the polymeric support.

Optionally, $R_1$ can be introduced by the reaction of the N-terminal end of the compound of the invention with a $R_1$—X compound, wherein $R_1$ has the aforementioned meaning and X is a leaving group, for example and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is —$OR_3$, —$NR_3R_4$ or —$SR_3$, with a complementary fragment which corresponds to the peptide of formula (I) in which $R_2$ is —OH in the presence of an adequate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the invention of general formula (I), wherein the fragments that have the functional groups not involved in the N—C bond formation are suitably protected with temporary or permanent protective groups, or alternatively other $R_2$ radicals may be introduced by simultaneous incorporation to the peptide cleavage process from the polymeric carrier.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxo-cyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (Trt tester), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino) benzyl ester (Dmab), among others; preferred protective groups of the invention are the All, tBu, cHex, Bzl and Trt esters.

The side chains of the trifunctional amino acids can be protected during the synthetic process with temporary or permanent protective groups orthogonal to the protective groups of the N-terminal and C-terminal ends.

The hydroxyl group of the tyrosine side chain can be protected with the 2-bromobenzyloxycarbonyl group (2-BrZ), tBu, All, Bzl or 2,6-dichlorobenzyl (2,6-diClZ) among others. The serine side chain is protected by a protective group selected from the group formed by tBu, Bzl, Trt and Ac. The histidine side chain can be protected by a protective group selected from the group formed by Tos, Dnp, methyl (Me), Boc, benzyloxymethyl (Bom), Bzl, Fmoc, Mts, Trt and Mtt. The amide group of the glutamine and asparagine side chain can be protected by the Trt group or the xanthyl group (Xan) or can be used unprotected. For the protection of the carboxyl group of the aspartic acid side chain esters can be used such as tBu ester, All ester, triphenylmethyl ester (Trt ester), cHx ester, Bzl ester, ortho-nitrobenzyl ester, para-nitrobenzyl ester, para-methoxybenzyl ester, trimethylsilylethyl ester, 2-phenylisopropyl ester, Fm ester or Dmab ester, among others. For the protection of the amino group of the lysine side chain amides can be used, such as amide acetate, amide benzoate, amide pivalate; carbamates, such as Cbz or Z, ClZ, pNZ, Boc, Troc, Teoc, Fmoc or Alloc, Trt, Mtt, Dnp, Dde, ivDde, Adpoc, among others.

In a preferred embodiment, the protective group strategy used is the strategy wherein the amino groups are protected by Boc, the carboxyl groups are protected by Bzl, cHx or All esters, the tyrosine side chain is protected with 2-BrZ or Bzl, the serine side chain is protected by the Bzl group, the histidine side chain is protected by the Tos or Bom group, the glutamic acid side chain is protected by Bzl, cHx or All, glutamine and asparagine are used unprotected in their side chain and the lysine side chain is protected by ClZ, Fmoc or Alloc.

In another preferred embodiment, the protective group strategy used is the strategy wherein the amino groups are protected by Fmoc, the carboxyl groups are protected by tBu, All or Trt esters, the tyrosine side chain is protected by tBu, the serine side chain is protected by the tBu group, the histidine side chain is protected by the Trt or Mtt group, the glutamic acid side chain is protected by tBu or All, glutamine and asparagine are used protected by the Trt group in its side chain, and the lysine side chain is protected by Boc, Trt or Alloc.

Examples of these and other protective groups, their introduction and removal, can be found in the literature [Atherton B. and Sheppard R. C., *"Solid Phase Peptide Synthesis: A practical approach"*, (1989), IRL Oxford University Press]. The term "protective groups" also includes the polymeric supports used in solid phase synthesis.

When synthesis takes place totally or partially in solid phase, the possible solid supports used in the process of the invention involve polystyrene support, polyethylene glycol grafted to polystyrene and similar, for example and not restricted to, p-methylbenzhydrylamine resins (MBNA) [Matsueda G. R. et al., *"A p-methylbenzhydrylamine resin for improved solid-phase synthesis of peptide amides"*, (1981), *Peptides*, 2, 45-50], 2-chlorotrityl resins [Barlos K. et al., *"Darstellung geschützter Peptid-Fragmente unter Einsatz substituierter Triphenylmethyl-Harze"*, (1989), *Tetrahedron Lett.*, 30, 3943-3946; Barlos K. et al., *"Veresterung von partiell geschützten Peptid-Fragmenten mit Harzen. Einsatz von 2-Chlorotritylchlorid zur Synthese von Leu1-Gastrin I"*, (1989), *Tetrahedron Lett.*, 30, 3947-3951], TentaGel™ resins (Rapp Polymere GmbH), ChemMatrix™ resins (Matrix Innovation, Inc.) and similar, which may or may not include a labile linker, such as 5-(4-aminomethyl-3,5-dimethoxyphenoxy) valeric acid (PAL) [Albericio F. et al., *"Preparation and application of the 5-(4-(9-fluorenylmethyloxycarbonyl) aminomethyl-3,5-dimethoxy-phenoxy) valeric acid (PAL) handle for the solid-phase synthesis of C-terminal peptide amides under mild conditions"*, (1990), *J. Org. Chem.*, 55, 3730-3743], 2-[4-aminomethyl-(2,4-dimethoxyphenyl)]phenoxyacetic acid (AM) [Rink H., "Solid-phase synthesis of protected peptide fragments using a trialkoxy-diphenyl-methylester resin", (1987), *Tetrahedron Lett.*, 28, 3787-3790], Wang [Wang S. S., *"p-Alkoxybenzyl Alcohol Resin and p-Alkoxybenzyloxycarbonylhydrazide Resin for Solid Phase Synthesis of Protected Peptide Fragments"*, (1973), *J. Am. Chem. Soc.*, 95, 1328-1333] and similar, which enable simultaneous deprotection and cleavage of the compound from the polymeric support.

Cosmetic or Pharmaceutical Compositions of the Invention

The compounds of the invention can be administered for their application by any means that causes contact between the compounds and the site of action in a mammal's body, preferably that of a human being, and in the form of a composition which contains them.

To this regard, another aspect of the invention is a cosmetic or pharmaceutical composition which comprises at least one compound of general formula (I), its stereoisomers, mixtures thereof, and/or its cosmetically or pharmaceutically acceptable salts together with at least one cosmetically or pharmaceutically acceptable adjuvant or excipient. These compositions can be prepared by conventional means known to persons skilled in the art [*"Harry's Cosmeticology"*, Seventh edition, (1982), Wilkinson J. B., Moore R. J., ed. Longman House, Essex, GB].

The compounds of this invention have variable solubility in water, according to the nature of their amino acid sequence or any possible modifications in the N-terminal and/or C-terminal ends. Therefore, the compounds of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerin, butylene glycol or polyethylene glycol or any combination thereof.

The cosmetically or pharmaceutically effective amount of the compounds of the invention which should be administered, as well as their dosage, will depend on numerous factors, including age, state of the patient, the nature or severity of the condition, disorder or disease to be treated and/or cared for, the route and frequency of administration and of the particular nature of the compounds to be used.

"Cosmetically and pharmaceutically effective amount" is understood to mean a non-toxic but sufficient amount of the compound or compounds of the invention to provide the desired effect. The compounds of the invention are used in the cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.00001% (in weight) and 10% (in weight) and even more preferably between 0.0001% (in weight) and 5% (in weight).

The compounds of general formula (I), their stereoisomers, mixtures thereof and/or their cosmetic or pharmaceutically acceptable salts, can also be incorporated into cosmetic or pharmaceutical delivery systems and/or sustained release systems.

The term "delivery systems" relates to a diluent, adjuvant, excipient or carrier with which the compound of the invention is administered. These cosmetic or pharmaceutical carriers can be liquids, such as water, oils or surfactants, including those of petroleum, animal, plant or synthetic origin, for example and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the compound of the invention can be administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems include, without restriction, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules and nanocapsules, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, microemulsions, more preferably water-in-oil microemulsions with an internal structure of reverse micelle and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part, and preferably should release a relatively constant quantity of the compounds of the invention. The amount of compound contained in the sustained release system will depend, for example, on where the composition is to be administered, the kinetics and duration of the release of the compound of the invention, as well as the nature of the condition, disorder and/or disease to be treated and/or cared for.

The compounds of this invention can also be adsorbed on solid organic polymers or solid mineral supports such as and not restricted to, talc, bentonite, silica, starch or maltodextrin among others.

The compositions which contain the compounds of general formula (I), their stereoisomers, mixtures thereof and/or their cosmetically or pharmaceutically acceptable salts can also be incorporated into fabrics, non-woven fabrics and medical devices which are in direct contact with the skin, thus releasing the compounds of the invention whether by biodegradation of the binding system to the fabric, non-woven fabric or medical device, or by friction between them and the body, due to bodily moisture, the skin's pH or body temperature. Furthermore, the compounds of the invention can be incorporated into the fabrics and non-woven fabrics used to make garments that are in direct contact with the body. Preferably, the fabrics, non-woven fabrics and medical devices containing the compounds of the invention are used for the treatment of conditions, disorders and/or diseases which improve or are prevented by the stimulation of the expression of proteins regulated by FOXO.

Examples of fabrics, non-woven fabrics, garments, medical devices and means for immobilizing the compounds to them, among which are the delivery systems and/or the sustained release systems described above, can be found in literature and are known in the prior art [Schaab C. K. (1986) HAPPI May 1986; Nelson G., "*Application of microencapsulation in textiles*", (2002), *Int. J. Pharm.,* 242(1-2), 55-62; "*Biofunctional Textiles and the Skin*" (2006) *Curr. Probl. Dermatol.* v.33, Hipler U. C. and Elsner P., eds. S. Karger A G, Basel, Switzerland; Malcolm R. K. et al., "*Controlled release of a model antibacterial drug from a novel self-lubricating silicone biomaterial*", (2004), *J. Cont. Release,* 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the compounds of the invention, their stereoisomers, mixtures thereof and/or their cosmetically or pharmaceutically acceptable salts, can be used in different types of compositions of topical or transdermal application which optionally include cosmetically or pharmaceutically acceptable excipients necessary for formulating the desired administration form. A person skilled in the art knows the different excipients which can be used in the cosmetic or pharmaceutical compositions which contain the compounds of the invention.

The compositions of topical or transdermal application can be produced in any solid, liquid or semisolid formulation, such as and not restricted to, creams, multiple emulsions such as and not restricted to, oil and/or silicone in water emulsions, water-in-oil and/or silicone emulsions, water/oil/water or water/silicone/water type emulsions and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories for example and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders among others.

The cosmetic or pharmaceutical compositions of the invention may include agents which increase the percutaneous absorption of the compounds of the invention, for example and not restricted to, dimethylsulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the peptide of the invention. The application area will be determined by the nature of the condition, disorder and/or disease to be treated and/or cared for.

Furthermore, the cosmetic compositions containing the compounds of general formula (I), their stereoisomers, mixtures thereof and/or their cosmetically or pharmaceutically acceptable salts can be used in different types of formulations for oral administration, preferably in the form of oral cosmetics or drugs, such as and not restricted to, capsules, including gelatin capsules, soft capsules, hard capsules, tablets, including sugar coated tablets, tablets, pills, powders, granules, chewing gum, solutions, suspensions, emulsions, syrups, elixirs, polysaccharide films, jellies or gelatins, and any other form known by the person skilled in the art. In a particular embodiment, the compounds of the invention can be incorporated into any form of functional food or fortified food, such as and not restricted to, dietary bars or compact or non-compact powders. These powders can be dissolved in water, soda, dairy products, soy derivatives or can be incorporated into dietary bars. The compounds of this invention can be formulated with common excipients and adjuvants for oral compositions or food supplements, for example and not restricted to, fat components, aqueous components, humectants, preservatives, texturizing agents, flavors, aromas, antioxidants and colorants common in the food industry.

Cosmetic or pharmaceutical compositions containing the compounds of general formula (I), their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal, subcutaneous, intradermal route, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the compounds of the invention can be administered.

Among the cosmetically or pharmaceutically acceptable adjuvants contained in the cosmetic or pharmaceutical compositions described in this invention are additional ingredients commonly used in cosmetic or pharmaceutical compositions, for example and not restricted to, other DNA protecting agents, other DNA repair agents, stem cell protecting agents, agents inhibiting neuronal exocytosis, anticholinergic agents, agents inhibiting muscular contraction, antiaging agents, anti-wrinkle agents, antiperspirant agents, anti-inflammatory and/or analgesic agents, anti-itching agents, calming agents, anesthetic agents, inhibitors of acetylcholine-receptor aggregation, inhibitors of acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, detoxifying agents, antihistamine agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, hydrolytic epidermal enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulation agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, AQP-3 modulating agents, aquaporin synthesis-stimulating agents, proteins of the aquaporin family, hyaluronic acid synthesis-stimulating agents, glycosaminoglycan synthesis-stimulating agents, fibronectin synthesis-stimulating agents, sirtuin synthesis-stimulating agents, sirtuin-activating agents, heat shock proteins, heat shock protein synthesis-stimulating agents, agents stimulating the synthesis of lipids and components of the stratum corneum, ceramides, fatty acids, agents that inhibit collagen degradation, agents that inhibit matrix metalloproteinase, agents that inhibit elastin degradation, agents that inhibit serine proteases such as kallikreins, elastase or cathepsin, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, a ntihyperkeratosis agents, comedolytic agents, anti-psoriatic agents, stabilizers, agents for the treatment and/or care of sensitive skin, firming agents, anti-stretch mark agents, binding agents, agents regulating sebum production, lipolytic agents or agents stimulating lipolysis, adipogenic agents, agents modulating PGC-1α expression, agents modulating the activity of PPARγ, agents which increase or reduce the triglyceride content of adipocytes, anti-cellulite agents, agents which inhibit PAR-2 activity, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, agents delaying hair loss, preservatives, perfumes, cosmetic and/or absorbent and/or body odor-masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof, provided they are physically and chemically compatible with the rest of components of the composition and in particular with the compounds of the invention. Furthermore, the nature of these additional ingredients should not unacceptably alter the benefits of the compounds of this invention. The nature of these additional ingredients can be synthetic or natural, such as plant extracts, or come from a biotechnological process or from a combination of a synthetic procedure and biotechnological process. Additional examples can be found in *CTFA International Cosmetic Ingredient Dictionary & Handbook*, 12*th Edition* (2008). In the context of this invention, biotechnological process is understood to be any process that produces the active ingredient, or part of it, in an organism, or in part of it.

In a particular embodiment, the anti-wrinkle agent and/or anti-aging agent is selected, for example and not restricted to, from the extracts or hydrolyzed extracts of *Vitis vinifera*, Rosa canina, Curcuma longa, Theobroma cacao, Ginkgo biloba, Leontopodium alpinum or Dunaliella salina among others, Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6™ [INCI: Glycerin, Water, Hydroxypropyl Cyclodextrin, Palmitoyl Tripeptide-38], Essenskin™ [INCI: calcium hydroxymethionine], Renovage™ [INCI: Teprenone], Resistem™ [INCI: Globularia Cordifolia Ferment], Dermaxyl® [INCI: Palmitoyl Oligopeptide], Calmosensine™ [INCI: Butylene Glycol, Acetyl Dipeptide-1 Cetyl Ester], Volulip™ [INCI: Cetearyl Ethylhexanoate, Sorbitan Isostearate, Portulaca Pilosa Extract, Sucrose Cocoate, Palmitoyl Tripeptide-38], Subliskin™ [INCI: Sinorhizobium Meliloti Ferment, Cetyl Hydroxyethyl Cellulose, Lecithin], Biopeptide CL™ [INCI: Palmitoyl Oligopeptide], Biopeptide EL™ [INCI: Palmitoyl Oligopeptide], Rigin™ [INCI: Palmitoyl Tetrapeptide-3], Biobustyl™ [INCI: Glyceryl Polymethacrylate, Rahnella/Soy Protein Ferment, Palmitoyl Oligopeptide], Dynalift™ [INCI: Sodium Polystyrene Sulfonate, Sorghum Bicolor Stalk Juice, Glycerin], Idealift™ [INCI: Acetyl Dipeptide-1 Cetyl Ester], Siegesbeckia [INCI: Siegesbeckia Orientales Extract], Ovaliss™ [INCI: Coco-glucoside, Caprylyl Glycol, Alcohol, Glaucine], Juvinity™ [INCI: Geranylgeranyisopropanol] or Resistem™ [INCI proposed: Globularia Cordifolia Ferment] marketed by Sederma/Croda, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate™ [INCI: Locust Bean (Ceratonia siliqua) Gum], Preregen® [INCI: Glycine soja (Soybean) Protein, Oxido Reductases], Pepha-Nutrix™ [INCI: Natural Nutrition Factors], Pepha-Tight™ [INCI: Algae Extract, Pullulan], Pentacare-NA™ [INCI: Hydrolyzed Wheat Gluten, Ceratonia Siliqua Gum], Syn®-Tacks [INCI: Glycerin, Palmitoyl Dipeptide-5 Diaminobutyloyl Hydroxythreonine, Palmitoyl Dipeptide-6 Diaminohydroxybutyrate], BeauActive™ MTP [INCI: Hydrolyzed milk protein], Syn®-TC [INCI: Tetradecyl Aminobutyroylvalylaminobutyric Urea Trifluoroacetate, Palmitoyl Tripeptide-5, Palmitoyl Dipeptide-5 Diaminobutyroyl Hydroxythreonine], Syn®-Hycan [INCI: Tetradecyl Aminobutyroylvalylaminobutyric Urea Trifluoroacetate], Syn®-Glycan [INCI: Tetradecyl Aminobutyroylvalyl-aminobutyric Urea Trifluoroacetate], Regu-Age™ [INCI: Hydrolyzed Rice Bran Protein, Oxido Reductases, Glycine Soja Protein], Pepha-Timp™ [INCI: Human oligopeptide-20], Colhibin [INCI: Hydrolyzed Rice Protein], Elhibin™ [INCI: Glycine Soja Protein, Disodium cocoamphodiacetate] or All-Q™ Plus [INCI: Ubiquinone, Tocopheryl Acetate] marketed by Pentapharm/DSM, Myoxinol™ [INCI: Hydrolyzed Hibiscus esculentus Extract], Syniorage™ [INCI: Acetyl Tetrapeptide-11], Dermican™ [INCI: Acetyl Tetrapeptide-9], DN-AGE® LS [INCI: Cassia alate leaf Extract], Hyalufix™ GL [INCI: Alpinia Galanga Leaf Extract], Neurobiox™ [INCI: Achillea Millefolium Extract], Deliner™ [INCI: Zea Mays (Corn) Kernel Extract], Lys'lastine™ V [INCI: Peucedanum Graveolens (Dill) Extract], Extracellium™ [INCI: Hydrolyzed Potato Protein], Proteasyl™ TP LS 8657 [INCI: Pisum Sativum Extract], Flavagrum™ PEG [INCI: PEG-6 Isostearate, Hesperetin Laurate], Micromerol™ [INCI: Pyrus Malus Fruit Extract], Extracellium™ [INCI: Hydrolyzed Potato Protein], Marine Filling Spheres [INCI: Pentaerythrityl Tetraisostearate, Silica Dimethyl Silylate, Sodium Chondroitin Sulfate, Atelocollagen], Triactigen™ [INCI: Mannitol, Cyclodextrin, Yeast Extract, Disodium Succinate], Eterniskin™ [INCI: Grifola Frondosa Fruiting Body Extract, Maltodextrin], Ascotide™ [INCI: Ascorbyl Phosphate Succinoyl Pentapeptide-12], Hyalurosmooth™ [INCI: Cassia Angustifolia Seed Polysaccharide], Indinyl™ [INCI: Cassia Angustifolia Seed Polysaccharide], Arganyl™ [INCI: Argania Spinosa Leaf Extract], Sphingoceryl Veg™ [INCI: Phyto-ceramides], Vit-A-Like™ [INCI: Vigna Acontifolia Seed Extract], Peptiskin™ [INCI: Arginine/Lysine polypeptide], Prodejine™ [INCI: Mannitol, Cyclodextrin, Yeast Extract, Disodium Succinate], Aqu'activ™ [INCI: Behenyl Alcohol, Glyceryl Oleate, Cocamide MIPA, Calcium Citrate], Elestan™ [INCI: Glycerin, Manilkara Leaf Extract], Hibiscin HP™ [INCI: Hibiscus Esculentus Seed Extract] or Litchiderm™ [INCI: Litchi Chinensis Pericarp Extract] marketed by Laboratoires Sérobiologiques/Cognis/BASF, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline® [INCI: Acetyl Hexapeptide-30], Aldenine® [INCI: Hydrolized Wheat Protein, Hydrolized Soy Protein, Tripeptide-1], Preventhelia® [INCI: Diaminopropionoyl Tripeptide-33], Decorinyl® [INCI: Tripeptide-10 Citrulline], Decorinol® [INCI: Tripeptide-9 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase® [INCI: Acetylarginyltriptophyl Diphenylglycine], Thermostressine® [INCI: Acetyl Tetrapeptide-22], Lipochroman™ [INCI: Dimethylmethoxy Chromanol], Chromabright® [INCI: Dimethylmethoxy Chromanyl Palmitate], Antarcticine® [INCI: Pseudoalteromonas Ferment Extract], dGlyage® [INCI: Lysine HCl, Lecithin, Tripeptide-9 Citrulline], Vilastene™ [INCI: Lysine HCl, Lecithin, Tripeptide-10 Citrulline], Hyadisine® [INCI: Pseudoalteromonas Ferment Extract], Hyanify™ [INCI: Saccharide Isomerate], Diffuporine® [INCI: Acetyl Hexapeptide-37], Silusyne® [INCI: Soybean (Glycine Soja) Oil, Sorbitan Sesquioleate, Isohexadecane, Sodium Hyaluronate, Lauryldimonium Hydroxypropyl Hydrolized Soy Protein, Acetyl Hexapeptide-39], Adifyline® [INCI: Acetyl Hexapeptide-38], Delisens™ [INCI: Acetyl Hexapeptide-46] or Telangyn™ [INCI: Acetyl Tetrapeptide-40] marketed by Lipotec/Lubrizol, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: Oryza sativa (Rice) Extract], D'Orientine™ IS [INCI: Phoenix dactylifera (Date) Seed Extract], Phytoquintescine™ [INCI: Einkorn (Triticum monococcum) Extract], Quintescine™ IS [INCI: Dipeptide-4], Peptide Vinci 01™ [INCI: Penta-decapeptide-1], Peptide Vinci 02™ [INCI: Hexapeptide-3], Aquarize IS™ [INCI: Hydrolyzed Rice Extract], Lanablue™ [INCI: Algae extract], Ederline™ [INCI: Pyrus Malus (Apple) Seed Extract], Dynachondrine™ ISR [INCI: Hydrolized Soy Protein], Prolixir S20™ [INCI: Dimer Tripeptide-43], Phytocohesine™ PSP [INCI: Sodium Beta-Sitosteryl Sulfate, Beta-Sitosterol], Perenityl™ IS [INCI: Pyrus Communis (Pear) Seed Extract], Caspaline 14™ [INCI: Hexapeptide-42], Peptide Q10™ [INCI: Pentapeptide-34 Trifluoroacetate], Survixyl IS™ [INCI: Pentapeptide-31], ChroNOgen™ [INCI: Tetrapeptide-26] or Telosense™ [proposed INCI: Hydrolized Soy Protein, Hydrolized Yeast Protein] marketed by Vincience/ISP/Ashland, BONT-L-Peptide™ [INCI: Palmitoyl Hexapeptide-19], TIMP Peptide [INCI: Acetylhexapeptide-20], ECM Moduline [INCI:

Palmitoyl Tripeptide-28], Renaissance™ [INCI: Hydrolyzed Wheat Protein, Palmitoyl Decapeptide-21, Decapeptide-22, Oligopeptide-78, Zinc Palmitoyl Nonapeptide-14] marketed by Infinitec Activos, Deepaline™ PVB [INCI: Palmitoyl hydrolyzed Wheat Protein], Sepilift® DPHP [INCI: Dipalmitoyl Hydroxyproline], Survicode™ [INCI: Sodium Cocoyl Alaninate], Aquaxyl™ [INCI: Xylitylglucoside, Anhydroxylitol, Xylitol] or Lipacide PVB™ [INCI: Palmitoyl hydrolyzed Wheat Protein] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] or Hematite [INCI: Hematite] marketed by Gattefossé, Thalassine™ [INCI: Algae Extract] marketed by Biotechmarine, ChroNOline™ [INCI: Caprooyl Tetrapeptide-3], Lanablue® [INCI: Algae Extract], Exo-H™ [INCI: *Alteromonas* Exopolysaccharide Extract], Exo-T™ [INCI: *Vibrio* Exopolysaccharide Extract], Hydriame® [INCI: Water, Glycosaminoglycans, *Sclerotium* Gum], MDI Complex® [INCI: Glycosaminoglycans], Adipofill™ [INCI: Ornithine, Phospholipids, Glycolipids] or Thymulen® 4 [INCI: Acetyl Tetrapeptide-2] marketed by Atrium/Unipex Innovations/Lucas Meyer Cosmetics, EquiStat™ [INCI: *Pyrus malus* Fruit Extract, *Glycine soja* Seed Extract], Juvenesce™ [INCI: Ethoxydiglicol and Caprylic Triglyceride, Retinol, Ursolic Acid, Phytonadione, Ilomastat], Ursolisome™ [INCI: Lecithin, Ursolic Acid, Atelocollagen, Xanthan Gum, Sodium chondroitin sulfate], Basaline™ [INCI: Hydrolyzed Malt Extract], Phytokine™ [INCI: Hydrolyzed Soy Protein], marketed by Coletica/Engelhard/BASF, Ameliox™ [INCI: Carnosine, Tocopherol, *Silybum marianum* Fruit Extract] or PhytoCellTec™ *Malus Domestica* [INCI: *Malus domestica* Fruit Cell Culture], Lipobelle™ Soyaglicane [INCI: Soy Isoflavones] or DermCom™ [INCI: *Crocus* Chrysanthus Bulb Extract, *Acacia* Senegal Gum, Aqua/Water] marketed by Mibelle Biochemistry, Bioxilift™ [INCI: Pimpinella anisum Extract], Papilactyl D™ [*Cyperus Esculentus* Tuber Extract], SMS Anti-Wrinkle® [INCI: *Annona squamosa* Seed Extract], Astressyl™ [INCI: *Salix Alba* (Willow) Leaf Extract], Pro-Coll-One+™ [INCI: Hydrolyzed Soy Protein], Ridulisse C™ [INCI: Soybean], Raffermine™ [INCI: Hydrolyzed Soy Flour], Toniskin™ [INCI: Yeast Extract] or Coheliss™ [INCI: Arabinoxylans purified from Rye Seeds], marketed by Silab, ActiMatrix™ [INCI: Peptide based mushroom Extract], Peptamide 6™ [INCI: Hexapeptide-11] marketed by Active Organics/Arch, HPS3™ [Paraffinum Liquidum, Padina Pavonica Thalllus Extract] marketed by Alban Muller, DermaPep A420™ [INCI: Myristoyl Tetrapeptide-6, Glycerin, Butylene Glycol] and DermaPep A350™ [INCI: Myristoyl Tripeptide-31, Butylene Glycol] marketed by Dermapep, Phytosphingosine SLC™ [INCI: Salicyloyl Phytosphingosine], TEGO Pep 4-17™ [INCI: Tetrapeptide-17], Granactive AGE™ [INCI: Palmitoyl Hexapeptide-14, *Lycium* Barbarum Fruit Extract (Goji Berry)], Sphingokine NP™ [INCI: Caprooyl Phytosphigonsine], TEGO Pep 4-Even™ [INCI: Glycerin, Tetrapeptide-30] marketed by Evonik Goldschmidt, Collageneer™ [INCI: *Helianthus Annuus* Seed Oil, *Lupinus Albus* Extract], Effipulp™ [INCI: Hydrolyzed Avocado Protein] or Actimp 1.9.3™ [INCI: Hydrolyzed Lupine Protein] marketed by Expanscience Laboratoires, ECM Protect™ [INCI: Tripeptide-2] or Glycosann™ [INCI: Sodium Chondroitin Sulfate] marketed by IEB, Ronacare™ Cyclopeptide-5 [INCI: Ectoin, Cyclopeptide-5] marketed by Merk, Ascotide™ [INCI: Ascorbyl Phosphate Succinoyl Pentapeptide-12] marketed by Peptron, Homeostatine™ [INCI: Enteromorpha *Compressa, Caesalpinia Spinosa*], Pronalen™ Firming [INCI: Lady's Thistle Extract, Lady's Mantle Extract, Horsetail Extract, Soy Germ Extract, Wheat Germ Extract, Alfalfa Extract, Radish Extract, Water (Aqua), Butylene Glycol, Decyl Glucoside] and Vitasource™ [INCI: Propanediol, Water, Baicalin] marketed by Provital, Reforcyl™ [INCI: Glutamine, Decyl Glucoside, Phenethyl Alcohol, Cistus *Incanus* Flower/Leaf/Stem Extract, Gynostemma Pentaphyllum Leaf/Stem Extract], Proteolea™ [INCI: Levan, Decyl Glucoside, *Olea Europaea* Leaf Extract, Phenethyl Alcohol, Zizyphus Jujuba Seed Extract] and Vitaderm™ [INCI: Hydrolyzed Rice Protein, *Ilex* Aquafolium Extract, Sodium Ursolate, Sodium Oleanolate] marketed by Rahn, Peptiskin™ [INCI: Arginine/Lysine polypeptide], Nuteline C™ [INCI: Hydrolyzed Hazelnut Protein] and Radicaptol™ [INCI: Propylene Glycol, Water, *Passiflora Incarnata* Extract, *Ribes Nigrum* Leaf Extract, *Vitis Vinifera* Leaf Extract] marketed by Solabia, StimulHyal [INCI: Calcium Ketogluconate], Dakaline™ [INCI: *Prunus* Amygdalus *Dulcis*, Anogeissus Leiocarpus Bark Extract], RenovHyal™ [INCI: Sodium Hyaluronate] and Viapure™ Boswellia [INCI: Boswellia *Serrata* Extract] marketed by Soliance, SymPeptide™ 222 [INCI: Myristoyl Pentapeptide-8], SymPeptide™ 225 [INCI: Myristoyl Pentapeptide-11], SymPeptide™ 239 [INCI: Myristoyl Octapeptide-1], SymPeptide™ 230 [INCI: Myristoyl Hexapeptide-4] marketed by Symrise, antagonists of the $Ca^{2+}$ channel for example and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes for example and not restricted to, photolyase or T4 endonuclease V, or chloride channel agonists among others, and/or mixtures thereof.

In another particular embodiment, the agent capable of filtering UV and IRA rays is selected, for example and not restricted to, from the group formed by photoprotectors of an organic or mineral nature active against ultraviolet A and/or B rays such as substituted benzotriazoles, substituted diphenyl acrylates, organic complexes of nickel, umbelliferone, urocanic acid, derivatives of biphenyl, e-stilbene, 3-benzylidene camphor, and their derivatives such as 3-(4-methylbenzylidene)camphor; derivatives of 4-aminobenzoic acid, 2-ethylhexyl 4-(dimethylamino)benzoate, 2-octyl 4-(dimethylamino)benzoate and amyl 4-(dimethylamino) benzoate; cinnamic acid esters, such as 2-ethylhexyl 4-methoxycinnamate or diethylamino hydroxybenzoyl hexyl benzoate, propyl 4-methoxycinnamate, isoamyl 4-methoxycinnamate, 2-ethylhexyl 2-cyano-3,3-phenyl cinnamate (octocrylenes); salicylic acid esters, such as 2-ethylhexyl salicylate, 4-isopropyl benzyl salicylate, homomenthyl salicylate; derivatives of benzophenone, such as 2-hydroxy-4-methoxybenzophenone, 2-hydroxy-4-methoxy-4'-methylbenzophenone, 2,2'-dihydroxy-4-methoxybenzophenone; benzalmalonic acid esters, such as di-2-ethylhexyl 4-methoxybenzalmalonate; derivatives of triazine, such as 2,4,6-trianilino, p-carbo-2'-ethyl-1'-hexyloxy-1,3,5-triazine, octyl triazone or dioctylbutamidotriazones; propane-1,3-diones, such as 1-(4-tert-butylphenyl)-3-(4'-methoxyphenyl)propane-1,3-dione; derivatives of ketotricyclo(5.2.1.0)decane; 2-phenylbenzimidazole-5-sulfonic acid; derivatives of benzophenone sulfonic acid, such as 2-hydroxy-4-methoxybenzophenone-5-sulfonic acid and its salts; 4-(2-oxo-3-bornylidenemethyl)benzenesulfonic acid, derivatives of benzoylmethane, such as benzoylmethane 2-methyl-5-(2-oxo-3-bornylidene)sulfonic acid, such as 1-(4'-tert-butylphenyl)-3-(4'-methoxyphenyl)propane-1,3-dione, 4-tert-butyl-4'-methoxydibenzoylmethane, 1-phenyl-3-(4'-isopropylphenyl)-propane-1,3-dione, compounds of enamine, anthranilates, silicones, derivatives of benzimidazole, imidazolines, derivatives of benzo allyl, Chromabright® [INCI: Dimethylmethoxy Chromanyl Palmitate] or Preventhelia® [INCI: Diaminopropionoyl Tripeptide-33] both marketed by Lipotec, metal oxides such as zinc, titanium, iron, zirconium, silicon, manganese, aluminum and cerium oxides; silicates, talc, barium sulfate, zinc stearate, carbon nanotubes and/or mixtures thereof.

In another particular embodiment, the whitening or depigmenting agent or melanin synthesis inhibiting agent, is selected, for example and not restricted to from the extracts of *Achillea millefolium, Aloe vera, Aradirachta indica, Asmuna japonica, Autocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domesticus, Pseudostellariae radix, Rumex crispus, Rumex occidentalis, Sapindus mukurossi, Saxifragia sarmentosa, Scutellaria galericulate, Sedum sarmentosum bunge, Stellaria medica, Triticum Vulgare, Arctostaphylos Uva ursi* or *Whitania somnifera* among others and/or Lipochroman™ [INCI: Dimethylmethoxy Chromanol], Chromabright® [INCI: Dimethylmethoxy Chromanyl Palmitate] marketed by Lipotec/Lubrizol, Whitami [INCI: Maltodextrin, Papain, Titanium Dioxide, *Angelica Acutiloba* Root Extract, Saposhnikovia *Divaricata* Root Extract, Thioctic Acid, Kaolin, Ascorbyl Glucoside, *Pinus Pinaster* Bark Oligomeric Proanthocyanidins] marketed by Alban Muller; NAB® Asafetida Extract [INCI: Aqua (Water), Butylene Glycol, Ethoxydiglycol, Ferula *Foetida* Extract] marketed by Arch; Licorice Roots Extract [INCI: Licorice (*Glycyrrhiza Glabra*) Extract] marketed by Campo Research; Belides™ [INCI: *Bellis Perennis* (Daisy) Flower Extract] marketed by CLR; Algowhite [INCI: Ascophyllum Nodosum Extract] marketed by Codif; Biowhite™ [INCI: Saxifraga Sarmentosa Extract, *Vitis Vinifera* (Grape) Fruit Extract, Butylene Glycol, Water, *Morus bombycis* Root Extract, Scutellaria *Baicalensis* Root Extract, Disodium EDTA], Melarrest® A [INCI: Glycerin, Lactic Acid, Kojic Acid, Ascorbic Acid], Melarrest® L [INCI: Water, Cyclopentasiloxane, Butylene Glycol, Propylene Glycol, Phospholipids, *Glycyrrhiza Glabra* (Liquorice) Extract, Kojic Acid, Ammonium Glycyrrhizate], Vitagen [INCI: Aminopropyl Ascorbyl Phosphate] or Collalift [INCI: Hydrolyzed Malt Extract], marketed by Coletica/Engelhard/BASF; DC Skin Bright™ [INCI: PEG-12 Glyceryl Distearate, Methyl Dihydroxybenzoate, Ethoxydiglycol, Polyethylene, Water] marketed by DC Ingredients; DS-WHITEKLE™ [INCI: Acetylphytosphingosine] marketed by Doosan; TEGO Cosmo C 250 [INCI: 1-methylhydantoin-2-imide] and TEGO Pep 4-Even [INCI: Glycerin, Tetrapeptide-30] marketed by Evonik Goldschmidt; Albatin® [INCI: Aminoethylphosphinic Acid, Butylene Glycol, Water] marketed by Exsymol; Synerlight™ [INCI: *Actinidia Chinensis* (Kiwi) Fruit Water, Butylene Glycol, Alcohol, *Sophora Angustifolia* Root Extract] marketed by Gattefossé; Clerilys™ [INCI: Water, *Cucumis* Santivus, *Morus Alba* Extract, *Hibiscus Sabdariffa* Extract, Wine Extract] marketed by Greentech; Melanostatine®-5 [INCI: Dextran, Nonapeptide-1] marketed by IEB/Unipex; Actiwhite™ [INCI: Water, Glycerin, Sucrose Dilaurate, Polysorbate 20, *Pisum Sativum* Extract], Active® Powder Whiteness [INCI: Water, Lauryl Methacrylate/Glycol Dimethacrylate Copolymer, Butylene Glycol, Dicaprylyl Ether, Titanium Dioxide, Algae, Citric Acid, Sodium Citrate, Waltheria Indica Leaf Extract, Ferulic Acid, Polyglyceryl-2-Dipolyhydroxystearate], Dermawhite® NF LS 9410 [INCI: Mannitol, Sodium Gluconate, Citric Acid, Sodium Citrate, Waltheria Indica Leaf Extract, Dextrin, Ferulic Acid], Radianskin™ [INCI: Hydroxyphenoxy Propionic Acid] marketed by L. Serobiologiques/Cognis/BASF; Lipobrite® HCA-4 [INCI: PEG-4, Hydroxycinnamic Acid] marketed by Lipochemicals; Whitessence™ [INCI: *Artocarpus Heterophyllus* Seed Extract, Maltodextrin, Disodium Phosphate, Sodium Phosphate] marketed by Lucas Meyer; Emblica™ [INCI: *Phyllanthus Emblica* Fruit Extract] marketed by Merck; SulforaWhite™ [INCI: *Lepidium Sativum* Sprout Extract, Glycerin, Lecithin, Phenoxyethanol, water], Delentigo™ [INCI: *Lepidium Sativum* Sprout Extract, Lecithin, Soy Isoflavones, Polysorbate 80, Alcohol, Glycerin, Phenoxyethanol, Water] marketed by Mibelle; Alpha-Arbutin [INCI: Alpha-arbutin], Gigawhite™ [INCI: Water, Glycerin, Malva *Sylvestris* (Mallow) Extract, *Mentha Piperita* Leaf Extract, *Primula* Veris Extract, Alchemilla Vulgaris Extract, *Veronica Officinalis* Extract, *Melissa Officinalis* Leaf Extract, *Achillea Millefolium* Extract], Melawhite® [INCI: Leukocyte Extract, AHA], Melfade®-J [INCI: Water, *Arctostaphylos Uva-Ursi* Leaf Extract, Glycerin, Magnesium Ascorbyl Phosphate] or Regu-Fade [INCI: Resveratrol] marketed by Pentapharm/DSM; CellActive® White [INCI: Water, Alcohol denat., Niacinamide, Zinc PCA, *Chlorella Vulgaris/Lupinus Albus* Protein Ferment, Nasturtium *Officinale* Extract] Illumiscin® [INCI: Glycerin, Aqua (Water), *Olea Europaea* Leaf Extract, Ascorbyl Glucoside, Zinc PCA] marketed by Rahn; Arlatone™ Dioic DCA [INCI: Octadecenedioic Acid, BHT], Etioline™ [INCI: Glycerin, Butylene Glycol, *Arctostaphylos Uva Ursi* Leaf Extract, Mitracarpus *Scaber* Extract], Lumiskin™ [INCI: Caprylic/Capric Triglyceride, Diacetyl Boldine], Melaclear™ 2 [INCI: Glycerin, Water, Dithiaoctanediol, Gluconic Acid, Sutilains, Beta-carotene], Lumisphere™ [INCI: Water (Aqua), Titanium Dioxide, Polysorbate 20, Cetyl Hydroxyethylcellulose, Polymethylmethacrylate, Trilaurin, Diacetyl boldine], O.D.A.White™ [INCI: Octadecenedioic Acid], Wonderlight™ [INCI: *Humulus Lupulus* (Hops) Strobile] marketed by Sederma/CRODA; Sepiwhite™ MSH [INCI: Undecylenoyl phenylalanine], Sepicalm™ VG [INCI: Sodium palmitoyl proline, Nymphaea Alba Flower Extract] marketed by Seppic; Clariskin II™ [INCI: *Triticum Vulgare* Extract], Dermalight® [INCI: *Tropaeolum Majus* Extract], Whitonyl® [INCI: Palmaria Palmata Extract] marketed by Silab; DermaPep A350 [INCI: Myristoyl Tripeptide-31, Butylene Glycol] or DermaPep W411™ [INCI: Palmitoyl Hexapeptide-36, Methyl Undecenoyl Leucinate, Butylene Glycol] marketed by Dermapep, Neurolight.61G™ [INCI: Glycerin, Water, Pancratium *Maritimum* Extract] marketed by Codif, Azeoglicina® [INCI: Potassium Azelaoyl Diglycinate] marketed by Sinerga; Whitesphere Premium [INCI: Sucrose Palmitate, Butylene Glycol, Glyceryl Linoleate, *Prunus* Amygdalus *Dulcis*, Almond Oil, Water (aqua), *Glycyrrhiza Glabra* (Liquorice) Root Extract, Magnesium Ascorbyl Phosphate, Undaria Pinnatifida Extract], Axolight™ [INCI: *Triticum Aestivum* Extract] marketed by Soliance; SymWhite® [INCI: Phenylethyl Resorcinol], Extrapone™ Nutgrass GW [INCI:*Cyperus Rotundus* Root Extract] marketed by Symrise; Synovea® HR [INCI:Hexylresorcinol] marketed by Sytheon; β-White [INCI: Water, Butylene Glycol, Hydrogenated Lecithin, Sodium Oleate, Oligopeptide-68, Disodium EDTA] marketed by Unipex; Achromaxyl™ [INCI: *Bras-* sica Napus Extract] marketed by Vincience/ISP; arbutin and its isomers, kojic acid and its derivatives, vitamin C and its derivatives, for example and not restricted to, 6-O-palmitoyl ascorbic acid, dipalmitoyl ascorbic acid, magnesium salt from ascorbic-2-phosphate acid (MAP), sodium from ascorbic-2-phosphate acid (NAP), ascorbyl glucoside or ascorbyl tetraisopalmitate (VCIP) among others, retinol and its derivatives, including tretinoin and isotretinoin, idebenone, hydroxybenzoic acid and its derivatives, flavonoids, soy extract, extract of lemon, extract of orange, extract of ginkgo, extract of cucumber, extract of geranium, extract of bearberry, extract of carob, extract of cinnamon, extract of marjoram, extract of rosemary, extract of clove, soluble extract of liquoritic, extract of blackberry leaf, niacinamide, liquiritin, resorcinol and its derivatives, hydroquinone, α-tocopherol, γ-tocopherol, azelaic acid, resveratrol, mercury salts, linoleic salts, α-lipoic acid, dihydrolipoic acid, alpha hydroxy acids, beta hydroxy acids, ellagic acid, ferulic acid, cinnamic acid, oleanolic acid, aloesin and its derivatives and/or inhibitors of serine protease activity, for example and not restricted to, inhibitors of tryptase, trypsin or PAR-2 activity, among others.

In another particular embodiment, the DNA protecting agent, the DNA repair agent, and/or stem cell protecting agent is selected, for example and not restricted to, from the group formed by GP4G SP [INCI: Water, Glycerin, Aretmia Extract], Heliostatine™ [INCI: Water, Glycerin, *Pisum Sativum* Extract], Orsirtine [INCI: Aqua, Glycerin, *Oryza Sativa* Extract], Chronogen™ [INCI: Water, Butylene Glycol, Tetrapeptide (INCI proposed)], Survixyl IS [INCI: Water, Butylene Glycol, Pentapeptide-31] and Chrondricare™ [INCI: Water, Butylene Glycol Pentapeptide-28] marketed by Vincience/ISP/Ashland; Lanacityn® [INCI: Glycerin, Aqua, *Alteromonas* ferment extract, Chysanthellum indicum extract] marketed by Atrium Innovations/Lucas Meyer Cosmetics; Repair Complex [INCI: *Bifida* Ferment Lysate] marketed by CLR; Phycojuvenine™ [INCI: *Laminaria Digitata*] marketed by Codif; Unirepair T-43™ [INCI: Butylene Glycol, Acetyl Tyrosine, Proline, Hydrolyzed Vegetable Protein, Adenosine Triphosphate] marketed by Induchem; Dragosine [INCI: Carnosine] marketed by Symrise; DN-Age [INCI: *Cassia Alata* Leaf Extract] marketed by Laboratories Serobiologiques/Cognis/BASF; Helioguard [INCI: *Porphyra* Umbilicalis encapsulated into liposomes], Phyto-CellTec *Malus Domestica* [INCI: PhytoCellTec *Malus Domestica*] or PhytoCellTec Argan [INCI: Argania *Spinosa* Sprout Cell Extract, Isomalt, Lecithin, Sodium Benzoate, Aqua] marketed by Mibelle Biochemistry; Pepha-Protect [INCI: Water Melon Extract] marketed by Pentapharm/DSM; Celligent™ [INCI: *Helianthus Annuus* Seed Oil, Ethyl Ferulate, Polyglyceryl-5 Trioleate, *Rosmarinus Officinalis* Leaf Extract, Aqua, Disodium Uridine Phosphate] or Defensil™ [INCI: Octyl Dodecanol, Echium Plantagineum Seed Oil, Cardiospermum Halicacabum Extract, *Helianthus Annuus* Seed Oil Unsaponifiables] marketed by Rahn; Venuceane™ [INCI: *Thermus Thermophilus* Ferment, Glycerin], UV-Soft [INCI: Yeast Extract], Renovage [INCI: Caprylic/Capric Triglyceride, Teprenone], Juvinity™ [INCI: Caprylic/Capric Triglyceride, Geranylgeranylpropanol (proposed)], Phytessence™ Holyherb [INCI: Butylene Glycol, Eriodictyon *Californicum* (Holyherb) Flower/Leaf/Stem Extract] or Resistem™ [INCI: Glycerin, *Globularia Cordifolia* Ferment] marketed by Sederma/Croda; and Heliomoduline™ [INCI: Low molecular weight peptides from cottonseed] or Stem-C-Guard [Hydrolyzed Pea] marketed by Silab.

In another particular embodiment, the reactive carbonyl species scavenger, free radical scavengers and/or anti-glycation agent, detoxifying agent, antioxidant and/or anti-pollution agent is selected, for example and not restricted to, from the group formed by carnosine and its derivatives, GHK [INCI: Tripeptide-1] and its salts and/or derivatives, Quintescine IS [INCI: Dipeptide-4] marketed by Vincience/ISP/Ashland; Melitane™ [INCI: Dextran, Acetyl Hexapeptide-1], Homeoxy [INCI: Enteromorpha *Compressa*, Palmaria Palmata Extract] or Lanatellis™ [INCI: Glycerin, Water, Chrysantellum Indicum Extract, *Camellia Sinensis* Leaf Extract] marketed by Atrium Innovations/Lucas Meyer Cosmetics; Protectan [INCI: *Lactococcus* Ferment Lysate] marketed by CLR; Phycosaccharide [INCI: Water, Hydrolyzed Algin, Magnesium Sulfate, Manganese Sulfate] or Algowhite™ [INCI: Water, Ascophyllum Nodosum Extract] marketed by Codif; Preregen™ [INCI: *Glycine Soja* (Soybean) Protein, Oxido Reductases], Edelweiss™ GC [INCI: Leontopodium *Alpinum* Extract], Lipogard™ [INCI: Squalane, Ubiquinone], Nectapure [INCI: Buddleja *Davidii* Extract, *Thymus Vulgaris* Extract], Alpaflor Nectapure [INCI: Buddleja *Davidii* Extract, *Thymus Vulgaris* Extract, Glycerin, Water] or Dismutin-BT™ [INCI: Highly purified SOD from a natural yeast strain of *Saccharomyces cerevisiae*] marketed by Pentapharm/DSM; TEGO Turmerone [INCI: *Curcuma Longa* Extract] marketed by Evonik Goldschmidt; Hierogaline [INCI: *Triticum Vulgare* (Wheat) germ oil unsaponifiables, *Sesamum Indicum* (Sesame) oil unsaponifiables] marketed by Expanscience Laboratoires; Glistin™ [INCI: Glutamylamidoethyl Indole, Water], Glutrapeptide™ [INCI: Water, Pyroglutamylamidoethyl Indole], Algisium C™ [INCI: Methylsilanol Mannuronate], Silysin C™ [INCI: Silanetriol Lysinate], Exsy-Arl™ [INCI: Prolinamidoethyl Imidazole, Butylene Glycol, Water] or OTZ-10™ [INCI: Water, Oxothiazolidine] marketed by Exsymol; Gatuline Skin-Repair Bio [INCI: Alcohol, Water, *Onopordum Acanthium* Flower/Leaf/Stem extract] marketed by Gattefossé; Preventhelia® [INCI: Diaminopropionoyl Tripeptide-33], Aldenine® [INCI: Hydrolized Wheat Protein, Hydrolized Soy Protein, Tripeptide-1], Lipochroman™ [INCI: Dimethylmethoxy Chromanol], Thermostressine® [INCI: Acetyl Tetrapeptide-22] or Bodyfensine® [INCI: Acetyl Dipeptide-3 Aminohexanoate] marketed by Lipotec/Lubrizol; Setiline™ [INCI: Hydrolyzed Trigonella Foenum-Graecum Seed Extract] marketed by Greentech; Sunactyl™ [INCI: Mannitol, *Pisum Sativum* Extract, Histidine HCl, Arginine, Cyclodextrin, Dextrin, Yeast Extract, Acetyl Tyrosine, Pyridoxine HCl, Khaya *Senegalensis* Bark Extract, Nicotinamide, Adenine Dinucleotide, Disodium Succinate, Aspartic Acid], Imidinyl™ [INCI: Tamarindus Indica Seed Polysaccharide], Phystrogene™ [INCI: Butylene Glycol, Malva *Sylvestris* (Mallow) Extract, Xanthan Gum] or Purisoft™ [INCI: Moringa Pterogysperma Seed Extract] marketed by Laboratoires Sérobiologiques/Cognis/BASF; AquaCacteen™ [INCI: Glycerin, Opuntia *Ficus* Indica Stem Extract, Phenoxyethanol, Aqua], Trimoist (KMF) [INCI: Sodium Stearoyl Lactylate, Letyl alcohol, Vegetable oil, Tocopheryl acetate, Glycerin, *Glycine soja* sterol, Sodium lactate, Sodium carboxymethyl betaglucan, Carnosine], MelanoBronze™ [INCI: Vitex Agnus Castus Extract (Monk's pepper berries extract (phyto-endorphins)), Acetyl Tyrosine], CM-Glucan [INCI: Sodium Carboxymethyl Betaglucan, Phenoxyethanol, SunActin™ [INCI: *Helianthus Annuus* (Sunflower) Sprout Extract, Tocopherols, Glycerin, Lecithin, Phenoxyethanol, Water], GSP-T skin [INCI: Glycerin, Alcohol, Water, PEG-40 Hydrogenated Castor Oil, *Vitis Vinifera* (Grape) Seed Extract] or Detoxophane™

[INCI: *Lepidium Sativum* Sprout Extract, Lecithin, Phenoxyethanol, Glycerin, Water] marketed by Mibelle Biochemistry; Bacocalmine™ [INCI: PEG-8, Bacopa Monniera Extract, Water (Aqua), Hydroxyethylcellulose], Kombuchka [INCI: *Saccharomyces/Xylinum* Black Tea Ferment, Glycerin, Hydroxyethyl cellulose] or Prodizia™ [INCI: *Albizia Julibrissin* Extract, Glycerin] marketed by Sederma/Croda; Extramel C [INCI: Hydroxypropyltrimonium Maltodextrin Crosspolymer, *Cucumis Melo* (Melon) Fruit Extract] marketed by Seppic; Defensine™ [INCI: *Triticum Vulgare* Germ Extract] or Antiglyskin™ [INCI: Water, *Helianthus Annuus* Seed Extract] marketed by Silab; ATP 23 [INCI: Azeloyl Tetrapeptide-23] marketed by Sinergia; Glycofilm [INCI: Biosaccharide Gum-4] marketed by Solabia.

Applications

In another aspect, this invention relates to a compound of general formula (I) as has been defined above, its stereoisomers, mixtures thereof and/or its cosmetically or pharmaceutically acceptable salts for its use in medicine, in particular for the treatment and/or prevention of cancer.

In another aspect, this invention relates to a compound of general formula (I) as has been defined above, its stereoisomers, mixtures thereof and/or its cosmetically or pharmaceutically acceptable salts for its use in the treatment of the skin, hair and/or mucous membranes.

In another aspect, this invention relates to the use of a compound of general formula (I) as has been defined above, its stereoisomers, mixtures thereof and/or its cosmetically or pharmaceutically acceptable salts for the cosmetic, non-therapeutic treatment and/or care of the skin, hair and/or mucous membranes. In particular for the treatment and/or prevention of the aging and/or photoaging of the skin, hair and/or mucous membranes.

In another aspect, this invention relates to a compound of general formula (I) as has been defined above, its stereoisomers, mixtures thereof and/or its cosmetically or pharmaceutically acceptable salts for its use in the prevention and/or delay of cell senescence and/or in the increase of cell longevity, in particular skin, hair and mucous membrane cells.

In another aspect, this invention relates to a compound of general formula (I) as has been defined above, its stereoisomers, mixtures thereof and/or its cosmetically or pharmaceutically acceptable salts for its use in DNA protection and/or repair of damaged DNA, in particular in DNA protection and/or repair of damaged DNA of the skin, hair and/or mucous membranes.

In another aspect, this invention relates to a compound of general formula (I) as has been defined above, its stereoisomers, mixtures thereof and/or its cosmetically or pharmaceutically acceptable salts for its use in the detoxification of ROS, in particular of ROS in the skin, hair and/or mucous membranes.

In another aspect, this invention relates to a compound of general formula (I) as has been defined above, its stereoisomers, mixtures thereof and/or its cosmetically or pharmaceutically acceptable salts for its use in the regulation of cell apoptosis, in particular in the inhibition or stimulation of cell apoptosis.

In another aspect, this invention relates to a compound of general formula (I) as has been defined above, its stereoisomers, mixtures thereof and/or its cosmetically or pharmaceutically acceptable salts for its use in the treatment of the inflammation, in particular inflammation in the skin and/or mucous membranes.

In another aspect, this invention relates to a compound of general formula (I) as has been defined above, its stereoisomers, mixtures thereof and/or its cosmetically or pharmaceutically acceptable salts for its use in the stimulation of the expression of proteins regulated by FOXO, preferably FOXO3 and in particular in the stimulation of the expression of proteins regulated by FOXO, preferably FOXO3 of the skin, hair and/or mucous membranes.

Alternatively, in another aspect, this invention relates to a method of treatment and/or prevention of the cancer which comprises the administration of a pharmaceutically effective amount of at least one compound of general formula (I) as has been defined above, its stereoisomers, mixtures thereof and/or its cosmetically or pharmaceutically acceptable salts.

In another aspect, this invention relates to a method of treatment and/or care of the skin, hair and/or mucous membranes which comprises the administration of a cosmetically or pharmaceutically effective amount of at least one compound of general formula (I) as has been defined above, its stereoisomers, mixtures thereof and/or its cosmetically or pharmaceutically acceptable salts. In particular for the treatment and/or prevention of the aging and/or photoaging of the skin, hair and/or mucous membranes.

In another aspect, this invention relates to a method of DNA protection and/or repair of damaged DNA which comprises the administration of a cosmetically or pharmaceutically effective amount of at least one compound of general formula (I) as has been defined above, its stereoisomers, mixtures thereof and/or its cosmetically or pharmaceutically acceptable salts. In particular, DNA protection and/or repair of damaged DNA in the skin, hair and/or mucous membranes.

In another aspect, this invention relates to a method of prevention and/or delay of cell senescence and/or in the increase of cell longevity which comprises the administration of a cosmetically or pharmaceutically effective amount of at least one compound of general formula (I) as has been defined above, its stereoisomers, mixtures thereof and/or its cosmetically or pharmaceutically acceptable salts. In particular, the prevention and/or delay of cell senescence and/or in the increase of cell longevity of the skin, hair and/or mucous membranes.

In another aspect, this invention relates to a method of detoxification of ROS which comprises the administration of a pharmaceutically or cosmetically effective amount of at least one compound of general formula (I) as has been defined above, its stereoisomers, mixtures thereof and/or its cosmetically or pharmaceutically acceptable salts. In particular, ROS in the skin, hair and/or mucous membranes.

In another aspect, this invention relates to a method of regulation of cell apoptosis which comprises the administration of a pharmaceutically or cosmetically effective amount of at least one compound of general formula (I) as has been defined above, its stereoisomers, mixtures thereof and/or its cosmetically or pharmaceutically acceptable salts. In particular, cell apoptosis in the skin and/or mucous membranes. In particular inhibition or stimulation of cell apoptosis.

In another aspect, this invention relates to a method of treatment of the inflammation which comprises the administration of a pharmaceutically or cosmetically effective amount of at least one compound of general formula (I) as has been defined above, its stereoisomers, mixtures thereof and/or its cosmetically or pharmaceutically acceptable salts. In particular, inflammation in the skin and/or mucous membranes.

In another aspect, this invention relates to a method of stimulation of the expression of proteins regulated by FOXO which comprises the administration of a pharmaceutically or cosmetically effective amount of at least one compound of general formula (I) as has been defined above, its stereoisomers, mixtures thereof and/or its cosmetically or pharmaceutically acceptable salts. Preferably FOXO is FOXO3 and in particular, it is found in the skin, hair and/or mucous membranes.

In a preferred embodiment, the damaged DNA is caused, for example and not restricted to, by radiation, contact with chemicals, cell malfunction and the exposure to magnetic fields. In particular, radiation is selected, for example and not restricted to, from the group formed by ultraviolet radiation, X rays, ionizing radiation and radioactivity. In particular, the chemicals which cause damage to the DNA are selected, for example and not restricted to, from the group formed by aromatic hydrocarbons, aromatic amines, asbestos, benzene, aflatoxins or vinyl chloride.

In a particular embodiment, the delay of cell senescence is a treatment and/or prevention of Alzheimer's disease, Parkinson's disease, Huntington's disease, stroke, dermal atrophy, elastolysis, wrinkles, sebaceous gland hyperplasia, senile lentigo, graying and hair loss, chronic skin ulcers, age-related deterioration of the wound healing capacity, degenerative joint diseases, osteoporosis, age-related deterioration of the immune system, age-related diseases of the vascular system including atherosclerosis, calcification, thrombosis, and aneurisms; and age-related macular degeneration.

In another aspect, the compounds of the invention can be administered by any means which causes contact of the compounds with the site of action in a mammal's body, preferably that of a human being, and more preferably in the form of a composition which contains them. The administration of the compounds of this invention is carried out by topical, transdermal, oral or parenteral application. In a more particular aspect the topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

The frequency of application or administration can vary greatly, depending on the needs of each subject, with a recommendation of an application from once a month to ten times a day, preferably from once a week to four times a day, more preferably from three times a week to twice a day, even more preferably once a day.

EXAMPLES OF EMBODIMENT

General Methodology

All the reagents and solvents are synthesis quality and are used without any additional treatment.

Abbreviations

The abbreviations used for amino acids follow the 1983 IUPAC-IUB Commission on Biochemical Nomenclature recommendations outlined in *Eur. J. Biochem.* (1984) 138: 9-37.

®, resin; 2-ClTrt-®, 2-chlorotrityl resin; Ac, acetyl; AM, 2-[4-aminomethyl-(2,4-dimethoxyphenyl)] phenoxyacetic acid; Asn, asparagine; BaP, benzo(α)pyrene; Boc, tert-butyloxycarbonyl; $CO_2$, carbon dioxide; CPD, cyclobutyl pyrimidine dimer; C-terminal, carboxy-terminal; DCM, dichloromethane; DIEA, N,N'-diisopropylethylamine; DIPCDI, N,N'-diisopropylcarbodiimide; DMF, N,N-dimethylformamide; DMSO, dimethylsulfoxide; DNA, deoxyribonucleic acid; D-PBS, Dulbecco's phosphate-buffered saline; ELISA, enzyme-linked immunosorbent assay; equiv, equivalent; ESI-MS, electrospray ionization mass spectrometry; FBS, fetal bovine serum; Fmoc, 9-fluorenylmethyloxycarbonyl; Gln, glutamine; Glu, glutamic acid; Gly, glycine; HCR, host cell reactivation; HDFa, human dermal fibroblasts, adult; HEKa, adult human epidermal keratinocytes; His, histidine; HOBt, 1-hydroxybenzotriazole; HPLC, high performance liquid chromatography; INCI, International Nomenclature of Cosmetic Ingredients; Leu, leucine; Lys, lysine; LSGS, low serum growth supplement; MBHA, p-methylbenzhydrylamine; Me, methyl; MeCN, acetonitrile; MED, minimal erythema dose; MeOH, methanol; N-terminal, amino-terminal; OTM, Olive Tail Moment; Palm, palmitoyl; PBS, phosphate buffered saline; Pro, proline; P/S, penicillin-streptomycin; q.s, quantity sufficient; q.s.p, quantity sufficient for; RLU, relative luminescence units; RPMI, culture medium; ROS, reactive oxygen species; SA-β-gal, senescence-associated β-galactosidase; Ser, serine; tBu, tert-butyl; TFA, trifluoroacetic acid; THF, tetrahydrofuran; Trt, triphenylmethyl or trityl; Tyr, tyrosine; UVA, ultraviolet radiation A; UVB, ultraviolet radiation B; UVC, ultraviolet radiation C; Val, valine.

Chemical Synthesis

All synthetic processes were carried out in polypropylene syringes fitted with porous polyethylene discs. All the reagents and solvents were synthesis quality and were used without any additional treatment. The solvents and soluble reagents were removed by suction. The Fmoc group was removed with piperidine-DMF (2:8, v/v) (1×1 min, 1×5 min, 5 mL/g resin) [Lloyd-Williams P. et al. (1997) "*Chemical Approaches to the Synthesis of Peptides and Proteins*" CRC, Boca Raton (FL, USA)]. Washes between stages of deprotection, coupling, and, again, deprotection, were carried out with DMF (3×1 min) each time using 10 mL solvent/g resin. Coupling reactions were performed with 3 mL solvent/g resin. The control of the couplings was performed by carrying out the ninhydrin test [Kaiser E. et al., "*Anal. Biochem*". (1970) 34: 595-598] or chloranil [Christensen T. "*Acta Chem. Scand*". (1979), 33B: 763-766]. All synthetic reactions and washes were carried out at 25° C.

The HPLC chromatographic analysis was carried out with Shimadzu equipment (Kyoto, Japan) using a reversed-phase column thermostatized at 30° C. (250×4.0 mm, Kromasil $C_8$, 5 µm, Akzo Nobel, Sweden). The elution was carried out using a gradient of acetonitrile (+0.07% TFA) in water (+0.1% TFA) at a flow rate of 1 mL/min and detection was carried out at 220 nm. The electrospray ionization mass spectrometry analysis was carried out in a WATERS Alliance ZQ 2000 detector using a mixture of MeCN:$H_2O$ 4:1 (+0.1% TFA) as the mobile phase and a flow rate of 0.3 mL/min.

Example 1

Prophetic

Obtaining Fmoc-$W_n$-$X_m$-$AA_1$-$AA_2$-$AA_3$-$AA_4$-$AA_5$-$AA_6$-$Y_p$-$Z_q$-O-2-ClTrt-®, wherein $AA_1$ is -L-Tyr-; $AA_2$ is -L-Asn- or -L-Tyr- or -L-Glu- or -L-His-; $AA_3$ is -L-Lys- or -L-Pro- or -L-Ser-; $AA_4$ is -Gly- or -L-His- or -L-Leu- or -L-Lys-; $AA_5$ is -L-Asn- or -L-Gln-; $AA_6$ is -L-Val-; and n, m, p and q are 0

8.8 mmol (1 equiv) of Fmoc-L-Val-OH dissolved in 55 mL of DCM, to which 0.85 equiv of DIEA is added, are incorporated into the 2-chlorotrityl (5.5 g; 8.8 mmol) dry resin. They are stirred for 5 min, after which 1.64 equiv of DIEA are added. The mixture is left to react for 40 min. The remaining chloride groups are blocked by treatment with 4.4 mL of MeOH.

The N-terminal Fmoc group is deprotected as described in the general methods and 2.5 equiv of Fmoc-L-Gln-OH or Fmoc-L-Asn-OH are coupled onto the peptidyl resin in the presence of 2.5 equiv of DIPCDI and 2.5 equiv of HOBt using DMF as a solvent for 1 hour. The resin is then washed as described in the general methods and the deprotection treatment of the Fmoc group is repeated to couple the next amino acid. Following the protocols described 2.5 equiv of Fmoc-Gly-OH or Fmoc-L-His(Trt)-OH or Fmoc-L-Leu-OH or Fmoc-L-Lys(Boc)-OH; 2.5 equiv of Fmoc-L-Lys(Boc)-OH or Fmoc-L-Pro-OH or Fmoc-L-Ser(tBu)-OH; 2.5 equiv of Fmoc-L-Asn-OH or Fmoc-L-Glu(tBu)-OH or Fmoc-L-His(Trt)-OH or Fmoc-Tyr(tBu)-OH; 2.5 equiv of Fmoc-L-Tyr(tBu)-OH are sequentially coupled in the presence of 2.5 equiv of HOBt and 2.5 equiv of DIPCDI.

After the synthesis, the peptidyl resins are washed with DCM (5×3 min) and dried by nitrogen stream.

Example 2

Obtaining Fmoc-$W_n$-$X_m$-$AA_1$-$AA_2$-$AA_3$-$AA_4$-$AA_5$-$AA_6$-$Y_p$-$Z_q$-AM-MBHA-®, Wherein $AA_1$ is -L-Tyr-; $AA_2$ is -L-Asn- or -L-Glu- or -L-His- or -L-Tyr-; $AA_3$ is -L-Lys- or -L-Pro- or -L-Ser-; $AA_4$ is -Gly- or -L-His- or -L-Leu- or -L-Lys-; $AA_5$ is -L-Asn- or -L-Gln-; $AA_6$ is -L-Val-; and n, m, p and q are 0

Weights have been normalized. 5 mmol of the Fmoc-AM-MBNA resin with a functionalization of 0.73 mmol/g were treated with piperidine-DMF according to the described general protocol in order to remove the Fmoc group. 2.5 equiv of Fmoc-L-Val-OH were incorporated onto the deprotected resin in the presence of 2.5 equiv of DIPCDI and 2.5 equiv of HOBt using DMF as a solvent for 1 hour.

The resin was then washed as described in the general methods and the deprotection treatment of the Fmoc group was repeated to couple the next amino acid. Following the protocols described 2.5 equiv of Fmoc-L-Gln-OH; 2.5 equiv of Fmoc-Gly-OH or Fmoc-L-His(Trt)-OH or Fmoc-L-Leu-OH or Fmoc-L-Lys(Boc)-OH; 2.5 equiv of Fmoc-L-Lys(Boc)-OH or Fmoc-L-Pro-OH or Fmoc-L-Ser(tBu)-OH; 2.5 equiv of Fmoc-L-Asn-OH or Fmoc-L-Glu(tBu)-OH or Fmoc-L-His(Trt)-OH or Fmoc-L-Tyr(tBu)-OH; 2.5 equiv of Fmoc-L-Tyr(tBu)-OH were sequentially coupled in the presence of 2.5 equiv of HOBt and 2.5 equiv of DIPCDI in each coupling. In place of 2.5 equiv of Fmoc-L-Gln-OH, 2.5 equiv of Fmoc-L-Asn-OH could have been used.

After synthesis, all the peptidyl resins were washed with DCM (5×3 min) and dried by nitrogen stream.

Example 3

General Process for Removal of Fmoc N-Terminal Protective Group

The N-terminal Fmoc group of the peptidyl resins obtained in example 2 was deprotected as described in the general methods (20% piperidine in DMF, 1×1 min+1×5 min). The peptidyl resins were washed with DMF (5×1 min), DCM (4×1 min), diethyl ether (4×1 min) and dried under vacuum. The same process could have been applied to the N-terminal Fmoc group of the peptidyl resin obtained in prophetic Example 1.

Example 4

Prophetic

Process for Introducing the $R_1$ Palmitoyl Group onto the Peptidyl Resins Obtained in Example 3

2.56 g of pre-dissolved palmitic acid (10 mmol; 10 equiv) in DMF (1 mL) are incorporated onto 1 mmol of the peptidyl resins in Example 3, in the presence of 1.53 g of HOBt (10 mmol; 10 equiv) and 1.56 mL of DIPCDI (10 mmol; 10 equiv). They are allowed to react for 15 hours, after which the resins are washed with THF (5×1 min), DCM (5×1 min), DMF (5×1 min), MeOH (5×1 min), DMF (5×1 min) THF (5×1 min), DMF (5×1 min), DCM (4×1 min), ether (3×1 min), and are dried under vacuum.

Example 5

Process for Introducing the $R_1$ Acetyl Group onto the Peptidyl Resins Obtained in Example 3

Weights have been normalized. 1 mmol of the peptidyl resins obtained in Example 3 was treated with 25 equiv of acetic anhydride in the presence of 25 equiv of DIEA using 5 mL of DMF as a solvent. They were left to react for 30 mins, after which the peptidyl resins were washed with DMF (5×1 min), DCM (4×1 min), diethyl ether (4×1 min) and were dried under vacuum.

Example 6

Cleavage Process from the Polymeric Support of the Peptidyl Resins Obtained in Examples 3, 4 and 5

Weights have been normalized. 200 mg of the dried peptidyl resins obtained in Example 5 were treated with 5 mL of TFA:$H_2O$ (95:5) for 2 hours at room temperature under stirring. The filtrates were collected onto 50 mL cold diethyl ether, they were filtered through polypropylene syringes fitted with porous polyethylene discs and washed 3 times with 50 mL diethyl ether. The final precipitates were dried under vacuum.

HPLC analysis of the obtained peptides in gradients of MeCN (+0.07% TFA) in $H_2O$ (+0.1% TFA) showed a purity exceeding 80% in all cases. The identity of the peptides obtained was confirmed by ESI-MS. The same procedures could have been applied to the peptidyl resins obtained in Examples 3 and 4.

Example 7

Prophetic

Cleavage Process of the Polymeric Support and Functionalization with $R_2$ Substituted Amine: Obtaining Ac-$W_n$-$X_m$-$AA_1$-$AA_2$-$AA_3$-$AA_4$-$AA_5$-$AA_6$-$Y_p$-$Z_q$—NH—$(CH_2)_{15}$—$CH_3$, Wherein $AA_1$ is -L-Tyr-; $AA_2$ is -L-Asn- or -L-Glu- or -L-His- or -L-Tyr-; $AA_3$ is -L-Lys- or -L-Pro- or -L-Ser-; $AA_4$ is -Gly- or -L-His- or -L-Leu- or -L-Lys-; $AA_5$ is -L-Asn- or -L-Gln-; $AA_6$ is -L-Val-; and n, m, p and q are 0

The compounds Ac-$W_n$-$X_m$-$AA_1$-$AA_2$-$AA_3$-$AA_4$-$AA_5$-$AA_6$-$Y_p$-$Z_q$—OH with fully protected side chains are obtained by treating 150 mg of the peptidyl resins Ac-$W_n$-$X_m$-$AA_1$-$AA_2$-$AA_3$-$AA_4$-$AA_5$-$AA_6$-$Y_p$-$Z_q$—O-2-ClTrt-® of Example 5, previously desiccated under vacuum in the presence of KOH, with 3 mL of a 3% solution of TFA in DCM for 5 min. The filtrates are collected onto 50 mL of cold diethyl ether and the treatment is repeated two times. The ethereal solutions are evaporated to dryness at reduced pressure and room temperature, the precipitates are redissolved in 50% MeCN in $H_2O$ and lyophilized. 10 mg of the obtained crude peptides are weighed in a flask and 3 equiv of hexadecylamine and 25 mL of anhydrous DMF are added. 2 equiv of DIPCDI are added, and left to react under magnetic stirring at 47° C. The reactions are monitored by HPLC until disappearance of the initial products, which are complete after 24-48 hours. The solvents are evaporated to dryness and co-evaporated twice with DCM. The obtained residues [Ac-$W_n$-$X_m$-$AA_1$-$AA_2$-$AA_3$-$AA_4$-$AA_5$-$AA_6$-$Y_p$-$Z_q$—NH—$(CH_2)_{15}$—$CH_3$ with fully protected side chains] are redissolved in 25 mL of a mixture of TFA:$H_2O$ (95:5) and left to react for 30 min at room temperature. 250 mL of cold diethyl ether are added, the solvents are evaporated under reduced pressure and two additional co-evaporations with ether are carried out. The residues are dissolved in a mixture of 50% MeCN in $H_2O$ and lyophilized.

Example 8

Stimulation of the Expression of Proteins Regulated by FOXO

The activation capacity of the FOXO response elements was evaluated in a human epithelial cell line stably transfected with the luciferase gene under the control of a regulatory sequence which contains different FOXO response elements which are in the promoters of the FOXO target genes. The activation capacity of the FOXO response elements indicates the expression of proteins regulated by FOXO. 30,000 cells per well were seeded in a total volume of 100 µL of RPMI 1640 culture medium. After 24 hours the cells with RPMI 1640 culture medium were washed and were incubated with the compounds of the invention at 0.5 mg/mL for 24 hours in a total volume of 100 µL per well. The carrier in which the compounds of the invention were dissolved was used (0.05% DMSO) as a negative control.

The measurement of the activity of the promoter was carried out using the Steady-Go Luciferase Assay System kit following the manufacturer's instructions. The luminescence values (RLU/sec) caused by the reaction between luciferase and the substrate were quantified with a luminometer and normalized by the cell number (absorbance at 630 nm), and the activity of the promoter was determined, which was standardized with regard to the negative control values.

Each experiment was carried out three times in 3 independent experiments.

TABLE 3

Stimulation of the activation of the FOXO response factors

| Treatment | Stimulation Average (%) |
|---|---|
| Carrier (0.05% DMSO) | 100 |
| 0.5 mg/mL Ac-L-Tyr-L-Asn-L-Lys-Gly-L-Gln-L-Val-$NH_2$ (Ac-SEQ ID NO: 1-$NH_2$) | 143 |
| 0.5 mg/mL Ac-L-Tyr-L-Glu-L-Ser-Gly-L-Gln-L-Val-$NH_2$ (Ac-SEQ ID NO: 16-$NH_2$) | 119 |
| 0.5 mg/mL Ac-L-Tyr-L-Asn-L-Pro-L-His-L-Gln-L-Val-$NH_2$ (Ac-SEQ ID NO: 18-$NH_2$) | 148 |
| 0.5 mg/mL Ac-L-Tyr-L-Glu-L-Pro-L-His-L-Gln-L-Val-$NH_2$ (Ac-SEQ ID NO: 40-$NH_2$) | 131 |
| 0.5 mg/mL Ac-L-Tyr-L-His-L-Pro-L-His-L-Gln-L-Val-$NH_2$ (Ac-SEQ ID NO: 28-$NH_2$) | 125 |
| 0.5 mg/mL Ac-L-Tyr-L-Tyr-L-Pro-L-His-L-Gln-L-Val-$NH_2$ (Ac-SEQ ID NO: 29-$NH_2$) | 120 |
| 0.5 mg/mL Ac-L-Tyr-L-Asn-L-Ser-L-His-L-Gln-L-Val-$NH_2$ (Ac-SEQ ID NO: 41-$NH_2$) | 129 |
| 0.5 mg/mL Ac-L-Tyr-L-Glu-L-Ser-L-His-L-Gln-L-Val-$NH_2$ (Ac-SEQ ID NO: 19-$NH_2$) | 145 |
| 0.5 mg/mL Ac-L-Tyr-L-His-L-Ser-L-His-L-Gln-L-Val-$NH_2$ (Ac-SEQ ID NO: 30-$NH_2$) | 138 |
| 0.5 mg/mL Ac-L-Tyr-L-Tyr-L-Ser-L-His-L-Gln-L-Val-$NH_2$ (Ac-SEQ ID NO: 20-$NH_2$) | 157 |
| 0.5 mg/mL Ac-L-Tyr-L-Asn-L-Lys-L-Leu-L-Gln-L-Val-$NH_2$ (Ac-SEQ ID NO: 21-$NH_2$) | 157 |
| 0.5 mg/mL Ac-L-Tyr-L-Glu-L-Lys-L-Leu-L-Gln-L-Val-$NH_2$ (Ac-SEQ ID NO: 22-$NH_2$) | 186 |
| 0.5 mg/mL Ac-L-Tyr-L-His-L-Lys-L-Leu-L-Gln-L-Val-$NH_2$ (Ac-SEQ ID NO: 25-$NH_2$) | 168 |
| 0.5 mg/mL Ac-L-Tyr-L-Tyr-L-Lys-L-Leu-L-Gln-L-Val-$NH_2$ (Ac-SEQ ID NO: 23-$NH_2$) | 174 |

TABLE 3-continued

Stimulation of the activation of the FOXO response factors

| Treatment | Stimulation Average (%) |
|---|---|
| 0.5 mg/mL Ac-L-Tyr-L-Asn-L-Lys-L-Lys-L-Gln-L-Val-NH$_2$ (Ac-SEQ ID NO: 8-NH$_2$) | 106 |
| 0.5 mg/mL Ac-L-Tyr-L-Tyr-L-Pro-L-Lys-L-Gln-L-Val-NH$_2$ (Ac-SEQ ID NO: 42-NH$_2$) | 133 |
| 0.5 mg/mL Ac-L-Tyr-L-Asn-L-Ser-L-Lys-L-Gln-L-Val-NH$_2$ (Ac-SEQ ID NO: 27-NH$_2$) | 128 |
| 0.5 mg/mL Ac-L-Tyr-L-Glu-L-Ser-L-Lys-L-Gln-L-Val-NH$_2$ (Ac-SEQ ID NO: 24-NH$_2$) | 133 |
| 0.5 mg/mL Ac-L-Tyr-L-His-L-Ser-L-Lys-L-Gln-L-Val-NH$_2$ (Ac-SEQ ID NO: 26-NH$_2$) | 124 |

Example 9

Identification of the Stimulative Capacity of the DNA Repair Pathways in Primary Keratinocytes The host cell reactivation (HCR) assay was used in HEKa primary keratinocytes to evaluate the capacity of the peptides of the invention to repair the damage to the DNA in a biologically functional way. 40,000 cells per well were seeded and they were co-transfected with a control plasmid which constitutively expresses the Firefly luciferase gene (pGL3), previously damaged by UVC, and with an undamaged plasmid which constitutively expresses the Renilla luciferase gene (vector pRluc-N1(h)).

Subsequently the cells were incubated with the compounds of the invention at 0.025 mg/mL and 0.5 mg/mL in EpiLife medium for 24 hours, after which the luminescence due to the activity of the Firefly and Renilla luciferases was measured using the Dual-Go Luciferase Assay System kit following the manufacturer's instructions. The carrier in which the compounds of the invention (EpiLife medium) were dissolved was used as a negative control. The activation percentage of the DNA repair for each sample was calculated standardizing the luminescence values of the Firefly luciferase with regard to the Renilla luciferase, subsequently standardizing with regard to the values of the negative control.

Each experiment was carried out three times in 3 independent experiments.

TABLE 4

Determination of the activation of DNA repair using the HCR assay in primary keratinocytes

| Treatment | Activation Average (%) |
|---|---|
| Basal | 100 |
| 0.025 mg/mL Ac-L-Tyr-L-Asn-L-Lys-Gly-L-Gln-L-Val-NH$_2$ (Ac-SEQ ID NO: 1-NH$_2$) | 150 |
| 0.025 mg/mL Ac-L-Tyr-L-Glu-L-Ser-L-His-L-Gln-L-Val-NH$_2$ (Ac-SEQ ID NO: 19-NH$_2$) | 191 |
| 0.025 mg/mL Ac-L-Tyr-L-Asn-L-Lys-L-Leu-L-Gln-L-Val-NH$_2$ (Ac-SEQ ID NO: 21-NH$_2$) | 231 |
| 0.025 mg/mL Ac-L-Tyr-L-Glu-L-Lys-L-Leu-L-Gln-L-Val-NH$_2$ (Ac-SEQ ID NO: 22-NH$_2$) | 203 |
| 0.025 mg/mL Ac-L-Tyr-L-Glu-L-Ser-L-Lys-L-Gln-L-Val-NH$_2$ (Ac-SEQ ID NO: 24-NH$_2$) | 295 |
| 0.5 mg/mL Ac-L-Tyr-L-Asn-L-Lys-Gly-L-Gln-L-Val-NH$_2$ (Ac-SEQ ID NO: 1-NH$_2$) | 290 |
| 0.5 mg/mL Ac-L-Tyr-L-Glu-L-Ser-L-His-L-Gln-L-Val-NH$_2$ (Ac-SEQ ID NO: 19-NH$_2$) | 304 |
| 0.5 mg/mL Ac-L-Tyr-L-Asn-L-Lys-L-Leu-L-Gln-L-Val-NH$_2$ (Ac-SEQ ID NO: 21-NH$_2$) | 357 |
| 0.5 mg/mL Ac-L-Tyr-L-Glu-L-Lys-L-Leu-L-Gln-L-VaI-NH$_2$ (Ac-SEQ ID NO: 22-NH$_2$) | 272 |
| 0.5 mg/mL Ac-L-Tyr-L-Glu-L-Ser-L-Lys-L-Gln-L-VaI-NH$_2$ (Ac-SEQ ID NO: 24-NH$_2$) | 271 |

Example 10

Determination of the Photoprotective Effectiveness of Ac-L-Tyr-L-Glu-L-Lys-L-Leu-L-Gln-L-Val-NH$_2$ (Ac-SEQ ID NO:22-NH$_2$) in Human Fibroblasts HDFa cells were put in culture medium for 24 hours in 96-well plates to form monolayers. Afterwards the cells were preincubated in darkness with 0.5 mg/mL, 0.1 mg/mL, 0.01 mg/mL of Ac-L-Tyr-L-Glu-L-Lys-L-Leu-L-Gln-L-Val-NH$_2$ (Ac-SEQ ID NO:22-NH$_2$) in PBS or PBS alone (control) for 1 hour at 37° C. and humidified air with 5% CO$_2$.

The cells were irradiated with a solar simulation lamp at ~60 J/cm$^2$ for 210 min at room temperature. A control plate was kept in the dark for the same time at room temperature. Once irradiation was completed the culture medium was changed for a new one and the plates were incubated for another 24 hours.

The cell viability was determined with the Neutral Red dye, measuring the absorbency at 540 nm in a spectrophotometer.

The photoprotective effectiveness was determined by comparing the viability obtained in cells treated with Ac-L-Tyr-L-Glu-L-Lys-L-Leu-L-Gln-L-Val-NH2 (Ac-SEQ ID NO:22-NH$_2$) with the irradiated and non-irradiated control cell response.

TABLE 5

Photoprotective effectiveness of Ac-L-Tyr-L-Glu-L-Lys-L-Leu-L-Gln-L-Val-NH$_2$ (Ac-SEQ ID NO: 22-NH$_2$)

| Treatment | Cell viability | Effectiveness Photoprotection (%) |
|---|---|---|
| Non-irradiated control | 99.85% | — |
| Irradiated control | 50.72% | — |
| 0.5 mg/mL Ac-SEQ ID NO: 22-NH$_2$ irradiated | 68.52% | 35.10 |
| 0.1 mg/mL Ac-SEQ ID NO: 22-NH$_2$ irradiated | 60.90% | 20.06 |
| 0.01 mg/mL Ac-SEQ ID NO: 22-NH$_2$ irradiated | 58.96% | 16.24 |

Example 11

Determination of the Photo Repair Effectiveness of Ac-L-Tyr-L-Glu-L-Lys-L-Leu-L-Gln-L-Val-NH$_2$ (Ac-SEQ ID NO:22-NH$_2$) in Human Fibroblasts HDFa cells were put in culture medium for 24 hours in 96-well plates to form monolayers at 37° C. and humidified air with 5% CO$_2$. Afterwards the culture medium was changed for D-PBS and the cells were irradiated with a solar simulation lamp at ~40 J/cm$^2$ for 180 min at room temperature. A control plate was kept in the dark for the same time at room temperature.

Afterwards 0.5 mg/mL, 0.1 mg/mL, 0.01 mg/mL of Ac-L-Tyr-L-Glu-L-Lys-L-Leu-L-Gln-L-Val-NH$_2$ (Ac-SEQ ID NO:22-NH$_2$) in culture medium or culture medium alone (control) were added to the cells and they were incubated for 24 hours in darkness at 37° C. and humidified air with 5% CO$_2$.

The cell viability was determined with the Neutral Red dye, measuring the absorbency at 540 nm in a spectrophotometer.

The photorepair effectiveness was determined by comparing the viability obtained in cells treated with Ac-L-Tyr-L-Glu-L-Lys-L-Leu-L-Gln-L-Val-NH$_2$ (Ac-SEQ ID NO:22-NH$_2$) with the irradiated and non-irradiated control cell response.

TABLE 6

Photo-repair effectiveness of Ac-L-Tyr-L-Glu-L-Lys-L-Leu-L-Gln-L-Val-NH$_2$ (Ac-SEQ ID NO: 22-NH$_2$)

| Treatment | Cell viability | Effectiveness Photo-repair (%) |
|---|---|---|
| Non-irradiated control | 99.96% | — |
| Irradiated control | 63.06% | — |
| 0.5 mg/mL Ac-SEQ ID NO: 22-NH$_2$ irradiated | 71.40% | 13.23 |
| 0.1 mg/mL Ac-SEQ ID NO: 22-NH$_2$ irradiated | 70.71% | 12.13 |
| 0.01 mg/mL Ac-SEQ ID NO: 22-NH$_2$ irradiated | 71.99% | 14.16 |

Example 12

Preparation of Liposomes Containing Ac-L-Tyr-L-Glu-L-Lys-L-Leu-L-Gln-L-Val-NH$_2$ (Ac-SEQ ID NO:22-NH$_2$)

In a suitable vessel water [INCI: WATER (AQUA)] and the peptide Ac-L-Tyr-L-Glu-L-Lys-L-Leu-L-Gln-L-Val-NH$_2$ (Ac-SEQ ID NO:22-NH$_2$) (phase A) were mixed together. The vessel was stirred in a bath at 50° C. The stirring continued until the peptide had completely dissolved.

Zemea Propanediol [INCI: PROPANEDIOL] and phenoxyethanol [INCI: PHENOXYETHANOL] (phase B) were added.

Parallely Emulmetik™ 930 [INCI: LECITHIN] was heated in a separate vessel under stirring at 50-60° C. Once at this temperature it was added to phase A+phase B.

The sample was passed, without cooling, through a microfluidifier for three cycles at an entry pressure of 80 bars and 15000 psi of exit pressure (3 cycles). Once microfluidified it was left stirring with a rotor until it reached room temperature. Table 7 shows the components which form the liposomes.

TABLE 7

Liposomes containing Ac-L-Tyr-L-Glu-L-Lys-L-Leu-L-Gln-L-Val-NH$_2$ (Ac-SEQ ID NO: 22-NH$_2$)

| Phase | Ingredients | % weight |
|---|---|---|
| A | WATER (AQUA) | q.s.p. 100 |
| A | Ac-SEQ ID NO: 22-NH$_2$ | 0.10 |
| B | PROPANEDIOL | 5.00 |
| B | PHENOXYETHANOL | 2.50 |
| C | LECITHIN | 0.50 |

Example 13

Preparation of Coacervation Capsules of Lipid Nanoparticles Containing Ac-L-Tyr-L-Glu-L-Lys-L-Leu-L-Gln-L-Val-NH$_2$ (Ac-SEQ ID NO:22-NH$_2$)

a) Preparation of a Microemulsion of the Compound Ac-L-Tyr-L-Glu-L-Lys-L-Leu-L-Gln-L-Val-NH$_2$ (Ac-SEQ ID NO:22-NH$_2$)

In a suitable the vessel the peptide Ac-L-Tyr-L-Glu-L-Lys-L-Leu-L-Gln-L-Val-NH$_2$ (Ac-SEQ ID NO:22-NH$_2$), water [INCI: WATER (AQUA)] and denaturalized ethyl alcohol [INCI: ALCOHOL DENAT] (phase A) were mixed together. The mixture was subjected to heavy stirring alternating with ultrasounds to dissolve the peptide. Prisorine™ 3505 [INCI: ISOSTEARIC ACID] and Docusate sodium USP [INCI: DIETHYLHEXYL SODIUM SULFOSUCCINATE] (phase B) were added under stirring. Lastly Finsolv-TN [INCI: C12-15 ALKYL BENZOATE] (phase C) was added. Once the components had been mixed together, the mixture was stirred until it reached room temperature. Table 8 shows the components that form the microemulsion.

TABLE 8

Microemulsion of Ac-L-Tyr-L-Glu-L-Lys-L-Leu-L-Gln-L-Val-NH$_2$ (Ac-SEQ ID NO: 22-NH$_2$)

| Phase | Ingredients | % weight |
|---|---|---|
| A | WATER (AQUA) | 10.00 |
| A | Ac-SEQ ID NO: 22-NH$_2$ | 0.75 |
| A | ALCOHOL DENAT | 8.00 |
| B | ISOSTEARIC ACID | 34.25 |
| B | DIETHYLHEXYL SODIUM SULFOSUCCINATE | 4.45 |
| C | C12-15 ALKYL BENZOATE | 42.55 | b) Preparation of a Microfluidified Emulsion of the Compound Ac-L-Tyr-L-Glu-L-Lys-L-Leu-L-Gln-L-Val-NH$_2$ (Ac-SEQ ID NO:22-NH$_2$).

In a suitable vessel water [INCI: WATER (AQUA)]; Zemea propanediol [INCI: PROPANEDIOL]; phenoxyethanol [INCI: PHENOXYETHANOL]; Structure XL [INCI: HYDROXYPROPYL STARCH PHOSPHATE]; Amigel™ [INCI: SCLEROTIUM GUM] and powdered hyaluronic acid [INCI: SODIUM HYALURONATE] (phase D) were mixed together. The vessel was placed in a bath at 70° C. under stirring.

Paralelly, in a separate vessel, the microemulsion described in section a) together with Massocare™ HD [INCI: ISOHEXADECANE], Montanov™ 68 [INCI: CETEARYL ALCOHOL, CETEARYL GLUCOSIDE] and Arlatone MAP 160 K [INCI: POTASSIUM CETYL PHOSPHATE] (phase E) were added, heating the mixture to 70-75° C. under stirring.

Phase E was slowly added to phase D under intense stirring. The heated sample was passed through a homogenizer at high pressure, microfluidifier, for 3 cycles at an entry pressure of 80 bars and 15000 psi of exit pressure, maintaining the operating temperature between 65 and 75° C. Once microfluidified the sample was stirred until room temperature was reached. Table 9 shows the components which form the microfluidified emulsion.

TABLE 9

Microfluidified emulsion Ac-L-Tyr-L-Glu-L-Lys-L-Leu-L-Gln-L-Val-NH$_2$ (Ac-SEQ ID NO: 22-NH$_2$)

| Phase | Ingredients | % weight |
|---|---|---|
| D | WATER (AQUA) | q.s.p. 100 |
| D | PROPANEDIOL | 5.48 |
| D | PHENOXYETHANOL | 2.85 |
| D | HYDROXYPROPYL STARCH PHOSPHATE | 0.33 |
| D | SCLEROTIUM GUM | 0.11 |
| D | SODIUM HYALURONATE | 0.01 |
| E | Microemulsion section a) | 7.32 |
| E | ISOHEXADECANE | 5.48 |
| E | CETEARYL ALCOHOL, CETEARYL GLUCOSIDE | 4.38 |
| E | POTASSIUM CETYL PHOSPHATE | 0.55 | c) Coacervation Capsules Containing a Microemulsion of Ac-L-Tyr-L-Glu-L-Lys-L-Leu-L-Gln-L-Val-NH$_2$ (Ac-SEQ ID NO:22-NH$_2$)

In a suitable vessel the emulsion from section b) was weighed and phase F of this section was constituted. In another vessel it was slowly added under stirring to water [INCI: WATER (AQUA)], Sensomer CI 50 [INCI: WATER (AQUA), STARCH HYDROXYPROPYLTRIMONIUM CHLORIDE, UREA, SODIUM LACTATE, SODIUM CHLORIDE, SODIUM BENZOATE] (phase G). Phase G was added to phase F under intense stirring. Structure XL [INCI: HYDROXYPROPYL STARCH PHOSPHATE] and Amigel [INCI: *SCLEROTIUM* GUM] (phase H) was added to this mixture very slowly and the mixture was maintained under intense stirring for 3 hours until it was completely dispersed.

Lastly Sepigel™ 305 [INCI: POLYACRYLAMIDE, WATER (AQUA), C13-14 ISOPARAFFIN, LAURETH-7] (phase I) was slowly added under stirring and the stirring was maintained for 30 min longer until a homogenous suspension was obtained. Table 10 shows the components that form the coacervation capsules.

TABLE 10

Lipid nanoparticle coacervation capsules with Ac-L-Tyr-LGlu-L-Lys-L-Leu-L-Gln-L-Val-NH$_2$ (Ac-SEQ ID NO: 22-NH$_2$)

| Phase | Ingredients | % weight |
|---|---|---|
| F | Emulsion section b) | 91.30 |
| G | WATER (AQUA) | 6.00 |
| G | SENSOMER Cl 50 [INCI: WATER (AQUA), STARCH HYDROXYPROPYLTRIMONIUM CHLORIDE, UREA, SODIUM LACTATE, SODIUM CHLORIDE, SODIUM BENZOATE] | 0.20 |
| H | HYDROXYPROPYL STARCH PHOSPHATE | 1.50 |
| H | SCLEROTIUM GUM | 0.75 |
| I | Sepigel ™ 305 [INCI: POLYACRYLAMIDE, WATER (AQUA), C13-14 ISOPARAFFIN, LAURETH-7] | 0.25 |

Example 14

Preparation of the Cosmetic Composition (Gel) Containing Ac-L-Tyr-L-Glu-L-Lys-L-Leu-L-Gln-L-Val-NH$_2$(Ac-SEQ ID NO:22-NH$_2$)

In a suitable vessel the components from phase A were added: water [INCI: WATER (AQUA)], propylene glycol USP [INCI: PROPYLENE GLYCOL], Hydrolite-5 2/016020 [INCI: PENTYLENE GLYCOL], Liponic™ EG-1 [INCI: GLYCERETH-26], glycerin USP [INCI: GLYCERIN] and Microcare™ BNA [INCI: BENZYL ALCOHOL]. Once it had all been added, Carbopol® Ultrez 10 [INCI: CARBOMER] was added little by little under stirring.

In a separate vessel, phase B was prepared: Thermostressine® solution [INCI: GLYCERIN, WATER (AQUA), ACETYL TETRAPEPTIDE-22], the compound Ac-L-Tyr-L-Glu-L-Lys-L-Leu-L-Gln-L-Val-NH$_2$ (Ac-SEQ ID NO:22-NH$_2$) previously dissolved in water [INCI: WATER (AQUA)] and butylene glycol [INCI: BUTYLENE GLYCOL] and Preventhelia® solution [INCI: WATER (AQUA), DIAMINOPROPIONOYL TRIPEPTIDE-33, CAPRYLYL GLYCOL].

Phase B was added to phase A under constant stirring.

In a separate vessel, phase C was prepared: Massocare TH [INCI: TRIETHYLHEXANOIN] and phenoxyethanol [INCI: PHENOXYETHANOL]. Once it had been prepared it was added to the mixture of phases A and B under constant stirring.

In a separate vessel, phase D was prepared: Kodasil™ KP-600 [INCI: ISODODECANE, VINYL DIMETHICONE, LAURYL DIMETHICONE CROSSPOLYMER, DIMETHICONE, LAURYL DIMETHICONE], Silicone DC 345 fluid [INCI: CYCLOMETHICONE] and Silicone DC 200 [INCI: DIMETHICONE]. Once it had been prepared it was added to the mixture of phases A, B and C under constant stirring. Afterwards phase E was added slowly: Silica bead SB-300 [INCI: SILICA, DIMETHICONE] under constant stirring until it was completely dissolved. Perfume tonus E20040401 [INCI: FRAGRANCE (PARFUM)] (phase F) was added and the solution was stirred. Finally the pH was adjusted to 6.0-6.5 with Sodium hydroxide 20% [INCI: SODIUM HYDROXIDE, WATER (AQUA)] (phase G). Table 11 shows the ingredients which comprise the formula:

TABLE 11

Cosmetic composition (gel) containing Ac-L-Tyr-L-Glu-L-Lys-L-Leu-L-Gln-L-Val-NH$_2$ (Ac-SEQ ID NO: 22-NH$_2$)

| Phase | Ingredients | % weight |
|---|---|---|
| A | WATER (AQUA) | 66.85 |
| A | PROPYLENE GLYCOL | 5.00 |
| A | PENTYLENE GLYCOL | 5.00 |
| A | GLYCERETH-26 | 3.00 |
| A | GLYCERIN | 2.00 |
| A | BENZYL ALCOHOL | 0.40 |
| A1 | CARBOMER | 0.20 |
| B | THERMOSTRESSINE ® SOLUTION (GLYCERIN, WATER (AQUA), ACETYL TETRAPEPTIDE-22) | |
| | GLYCERIN | 1.90 |
| | WATER (AQUA) | 0.099 |
| | ACETYL TETRAPEPTIDE-22 | 0.001 |
| B | Ac-SEQ ID NO: 22-NH$_2$ | 0.001 |
| B | BUTYLENE GLYCOL | 1.60 |
| B | WATER (AQUA) | 0.399 |
| B | PREVENTHELIA ® SOLUTION (WATER (AQUA), DIAMINOPROPIONYL TRIPEPTIDE-33, CAPRYLYL GLYCOL) | |
| | WATER (AQUA) | 0.9945 |
| | DIAMINOPROPIONYL TRIPEPTIDE-33 | 0.0050 |
| | CAPRYLYL GLYCOL | 0.0005 |
| C | TRIETHYLHEXANOIN | 3.00 |
| C | PHENOXYETHANOL | 0.90 |
| D | KODASIL KP-60 ™ (ISODODECANE, VINYL DIMETHICONE, LAURYL DIMETHICONE CROSSPOLYMER, DIMETHICONE, LAURYL DIMETHICONE) | |
| | ISODODECANE | 1.8600 |
| | VINYL DIMETHICONE, LAURYL DIMETHICONE CROSSPOLYMER | 0.4275 |
| | DIMETHICONE | 0.3563 |
| | LAURYL DIMETHICONE | 0.3563 |
| D | CYCLOMETHICONE | 1.00 |
| D | DIMETHICONE | 0.50 |
| E | SILICA BEAD SB-300 (SILICA, DIMETHICONE) SILICA | 3.72 |
| | DIMETHICONE | 0.28 |
| F | FRAGRANCE (PARFUM) | 0.15 |
| G | SODIUM HYDROXIDE, WATER (AQUA)) | q.s.p. pH 6.0-6.5 |

Example 15

Preparation of a Cosmetic Composition (Cream) Containing Ac-L-Tyr-L-Glu-L-Lys-L-Leu-L-Gln-L-Val-NH$_2$ (Ac-SEQ ID NO:22-NH$_2$)

In a vessel suitable for all the contents the components of phase A were dissolved: water [INCI: WATER (AQUA)], Hydrolite-5 2/016020 [INCI: PENTYLENE GLYCOL], glycerin USP [INCI: GLYCERIN], Betafin BP™ [INCI: BETAINE] and Microcare BNA™ [INCI: BENZYL ALCOHOL]. Once it had all been added, Carbopol® Ultrez 10 [INCI: CARBOMER] was added little by little under stirring until it had dissolved. Arlatone Map 160 K™ [INCI: POTASSIUM CETYL PHOSPHATE] was added until dispersed and the mixture was heated to 70-75° C.

In a separate vessel, phase B was mixed: Phytocream 2000™ [INCI: GLYCERYL STEARATE, CETEARYL ALCOHOL, POTASSIUM PALMITOYL HYDROLYZED WHEAT PROTEIN], Massocare TH™ [INCI: TRIETHYLHEXANOIN], Finsolv-TN™ [INCI: C12-15 ALKYL BENZOATE], Polyiso 200™ [INCI: HYDROGENATED POLYISOBUTENE], Silicone DC 345 fluid [INCI: CYCLOMETHICONE], cetearyl alcohol [INCI: CETEARYL ALCOHOL] and phenoxyethanol [INCI: PHENOXYETHANOL]. It was heated to 70-75° C. and was slowly added to phases A, A1 and A2 under stirring with a turbine. It was left to cool to 50° C.

In a separate vessel, phase C was prepared: the compound Ac-L-Tyr-L-Glu-L-Lys-L-Leu-L-Gln-L-Val-NH$_2$ (Ac-SEQ ID NO:22-NH$_2$) previously dissolved in water [INCI: WATER (AQUA)] and butylene glycol [INCI: BUTYLENE GLYCOL] and Antarcticine® C solution [INCI: WATER (AQUA), *PSEUDOALTEROMONAS* FERMENT EXTRACT, CAPRYLYL GLYCOL]. It was slowly added to phases A, A1, A2 and B under stirring. Sepigel 305 [INCI: POLYACRYLAMIDE, WATER (AQUA), C13-14 ISOPARAFFIN, LAURETH-7] (phase D) was added stirring with a rotor until homogenization of the mixture was achieved. The perfume Tonus E20040401 (phase E) [INCI: FRAGRANCE (PARFUM)] was added, stirring with a rotor. The pH was adjusted to 6.0-6.5 with sodium hydroxide 20% [INCI: SODIUM HYDROXIDE, WATER (AQUA)] (phase F). Once the pH had been adjusted Aristoflex AVC™ [INCI: AMMONIUM ACRYLOYLDIMETHYLTAURATE/VP COPOLYMER] (phase G) was added slowly under stirring until the sample was homogenized. Table 12 shows the ingredients of the formula:

TABLE 12

Cosmetic composition (cream) containing Ac-L-Tyr-L-Glu-L-Lys-L-Leu-L-Gln-L-Val-NH$_2$ (Ac-SEQ ID NO: 22-NH$_2$)

| Phase | Ingredients | % weight |
|---|---|---|
| A | WATER (AQUA) | 68.05 |
| A | PENTYLENE GLYCOL | 5.0 |
| A | GLYCERIN | 3.00 |
| A | BETAINE | 3.00 |
| A | BENZYL ALCOHOL | 0.40 |
| A1 | CARBOMER | 0.30 |
| A2 | POTASSIUM CETYL PHOSPHATE | 2.00 |
| B | TRIETHYLHEXANOIN | 2.00 |
| B | C12-15 ALKYL BENZOATE | 2.00 |
| B | HYDROGENATED POLYISOBUTENE | 2.00 |
| B | CYCLOMETHICONE | 1.50 |
| B | CETEARYL ALCOHOL | 1.00 |
| B | PHENOXYETHANOL | 0.90 |
| B | PHYTOCREAM 2000 (GLYCERYL STEARATE, CETEARYL ALCOHOL, POTASSIUM PALMITOYL HYDROLYZED WHEAT PROTEIN) | |
| | GLYCERYL STEARATE | 1.65 |
| | CETEARYL ALCOHOL | 1.65 |
| | POTASSIUM PALMITOYL HYDROLYZED WHEAT PROTEIN | 0.70 |
| C | Ac-SEQ ID NO: 22-NH$_2$ | 0.001 |
| C | BUTYLENE GLYCOL | 1.600 |
| C | WATER (AQUA) | 0.399 |
| C | ANTARCTICINE ® C SOLUTION (WATER (AQUA), PSEUDOALTEROMONAS FERMENT EXTRACT, CAPRYLYL GLYCOL) | |
| | WATER (AQUA) | 1.4925 |
| | PSEUDOALTEROMONAS FERMENT EXTRACT | 0.5000 |
| | CAPRYLYL GLYCOL | 0.0075 |
| D | SEPIGEL ™ 305 (POLYACRYLAMIDE, WATER (AQUA), C13-14 ISOPARAFFIN, LAURETH-7) | |
| | POLYACRYLAMIDE | 0.20 |
| | WATER (AQUA) | 0.17 |
| | C13-14 ISOPARAFFIN | 0.10 |
| | LAURETH-7 | 0.03 |
| G | AMMONIUM ACRYLOYLDIMETHYLTAURATE/ VP COPOLYMER | 0.20 |
| E | FRAGRANCE (PARFUM) | 0.15 |
| F | SODIUM HYDROXIDE 20% (SODIUM HYDROXIDE, WATER (AQUA) | q.s.p. pH 6.0 –6.5 |

Example 16

Determination of the Effectiveness of Ac-L-Tyr-L-Glu-L-Lys-L-Leu-L-Gln-L-Val-NH$_2$ (Ac-SEQ ID NO:22-NH$_2$) in the Reduction of Cell Senescence in Human Fibroblasts A widely used assay to evaluate cell senescence is histochemical detection of the activity, of the β-galactosidase, called SA-β-Gal. The activity of the β-galactosidase is derived from the increase in the lysosomal content of senescent cells, which enables the detection of the lysosomal β-galactosidase at pH 6.0. The β-galactosidase is considered a marker of senescence both in vitro and in vivo.

With this objective, HDFa cells from phase 4 of a 55-year-old person were seeded in 96-well plates at 10,000 cells/well in culture medium 106 supplemented with 2% LSGS. After 24 hours the culture medium was removed and the cells were treated with 0.025 mg/mL and 0.01 mg/mL of Ac-L-Tyr-L-Glu-L-Lys-L-Leu-L-Gln-L-Val-NH$_2$ (Ac-SEQ ID NO:22-NH$_2$) in culture medium 106 for another 24 hours at 37° C. and humidified air with 5% CO$_2$.

As a positive control of cell senescence (old fibroblasts) HDFa from phase 3 of a 67-year-old person were used treated with culture medium; as a negative control of cell senescence (juvenile fibroblasts) HDFa from phase 4 were used from a 37-year-old person treated with culture medium.

After the incubation period the activity of the senescence-associated β-galactosidase (SA-β-Gal) was determined with the Senescence Cells Histochemical Kit.

TABLE 13

Effectiveness of Ac-L-Tyr-L-Glu-L-Lys-L-Leu-L-Gln-L-Val-NH2 (Ac-SEQ ID NO: 22-NH$_2$) on the reduction of cell senescence

| Treatment | Proportion of positive SA-β-gal cells |
|---|---|
| Positive senescence control (HDF 67-year-old) | 72.40 |
| Negative senescence control (HDF 37-year-old) | 0.59 |
| Control (HDF 55-year-old) | 27.28 |
| 0.025 mg/mL Ac-SEQ ID NO: 22-NH$_2$ (HDF 55-year-old) | 16.90 |

TABLE 13-continued

Effectiveness of Ac-L-Tyr-L-Glu-L-Lys-L-
Leu-L-Gln-L-Val-NH2 (Ac-SEQ ID NO: 22-NH$_2$)
on the reduction of cell senescence

| Treatment | Proportion of positive SA-β-gal cells |
|---|---|
| 0.01 mg/mL Ac-SEQ ID NO: 22-NH$_2$ (HDF 55-year-old) | 7.02 |

The compound Ac-SEQ ID NO:22-NH$_2$ reduced the proportion of cells containing β-galactosidase, which is interpreted as a delay in cell senescence.

Example 17

Determination of the Protective Effectiveness of Ac-L-Tyr-L-Glu-L-Lys-L-Leu-L-Gln-L-Val-NH$_2$ (Ac-SEQ ID NO:22-NH$_2$) Against Genotoxicity Induced by Benzo[a]pyrene (BaP) Photo Activated in Human Fibroblasts Applying the Alkaline Comet Assay Benzo[a]pyrene is an aromatic polycyclic hydrocarbon present in pollution, which is potentially genotoxic due to the fact that it metabolizes in carcinogenic compounds which inserts themselves in DNA interfering in the transcription processes.

Fibroblasts from a sample of human skin were isolated and incubated with 0.01 mg/mL of Ac-L-Tyr-L-Glu-L-Lys-L-Leu-L-Gln-L-Val-NH$_2$ (Ac-SEQ ID NO:22-NH$_2$) or carrier (control) with and without the presence of 40 μM BaP for 2 hours at 37° C. Once this contact time was over the cells were irradiated with 90 KJ/m$^2$ UVA/visible light (320-800 nm) for a maximum of 2 min at 4° C. to induce photo activation of BaP which damages the DNA. This damage was analyzed by the alkaline comet assay, detecting the DNA breakages. The protective effectiveness of the damage to the DNA of the different treatments was determined by analyzing the images using the software Fenestra Komet 5.5, expressing the damage to the DNA as the Olive Tail Moment (OTM; arbitrary units) and the $\chi^2$ OTM function was determined, related to the quantity of damaged DNA, with the software TableCurve 2D.

As a negative control all the non-irradiated treatments were included (control, 40 μM BaP, 0.01 mg/mL of Ac-SEQ ID NO:22-NH$_2$ and 0.01 mg/mL of (Ac-SEQ ID NO:22-NH$_2$)+40 μM BaP). In table 14 the protective effectiveness results of Ac-SEQ ID NO:22-NH$_2$ in human fibroblasts are shown.

TABLE 14

Protective effectiveness of Ac-L-Tyr-L-Glu-L-Lys-
L-Leu-L-Gln-L-Val-NH$_2$ (Ac-SEQ ID NO: 22-NH$_2$)
against the damage to the DNA
induced by BaP in human fibroblasts
Treatment

| Ac-SEQ ID NO: 22-NH$_2$ | BaP | Irradiation with UVA/visible | $\chi^2$ OTM |
|---|---|---|---|
| no | no | no | 2.08 |
| no | 40 μM | no | 2.07 |
| 0.01 mg/mL | no | no | 2.26 |
| 0.01 mg/mL | 40 μM | no | 2.18 |
| no | no | yes | 2.25 |
| no | 40 μM | yes | 11.38 |
| 0.01 mg/mL | no | yes | 2.09 |
| 0.01 mg/mL | 40 μM | yes | 3.52 |

The protection percentage conferred by the compound Ac-SEQ ID NO:22-NH$_2$ against DNA damage induced by BaP was shown as the relationship of the value of $\chi^2$ OTM for treatment with the compound Ac-SEQ ID NO:22-NH$_2$ in the presence of photo-activated BaP with regard to the value of $\chi^2$ OTM of the treatment with photo-activated BaP according to the formula resulting in a protection percentage conferred by the compound Ac-SEQ ID NO:22-NH$_2$ against damage to DNA induced by BaP of 84.3%.

$$\% \text{ Protection} = \left[1 - \frac{(\chi^2 OTM_{compound+BaP+radiation} - \chi^2 OTM_{compound+radiation})}{(\chi^2 OTM_{BaP+radiation} - \chi^2 OTM_{radiation})}\right] \times 100$$

Example 18

Preparation of a Cosmetic Composition Containing Ac-L-Tyr-L-Glu-L-Lys-L-Leu-L-GM-L-Val-NH$_2$(Ac-SEQ ID NO:22-NH$_2$)

In a suitable vessel for the whole contents the components of phase A were dissolved: Purified water [INCI: WATER (AQUA)], Hydrolite-5 [INCI: PENTYLENE GLYCOL], glycerin USP [INCI: GLYCERIN] and Microcare BNA [INCI: BENZYL ALCOHOL]. Once it was all incorporated, Amigel [INCI: *SCLEROTIUM* GUM] was added little by little (phase A1) under stirring until dispersion. Next xanthan gum [INCI: XANTHAN GUM] was added (phase A2) until dispersion and the mixture was heated to 70-75° C.

In a separate vessel, phase B was mixed together: Glyceryl stearate [INCI: GLYCERYL STEARATE], cetearyl alcohol [INCI: CETEARYL ALCOHOL], synthetic squalane [INCI: HYDROGENATED POLYISOBUTENE], alpha-bisabolol [INCI: BISABOLOL], Dermofeel SL™ [INCI: SODIUM STEAROYL LACTYLATE], Dermofeel PS™ [INCI: POLYGLYCERYL-3 STEARATE], phenoxyethanol [INCI: PHENOXYETHANOL], Cetiol SB-45™ [INCI: SHEA BUTTER (BUTYROSPERMUM PARKII)] and polysorbate 20 [INCI: POLYSORBATE 20]. It was heated to 70-75° C. and was slowly added to phases A, A1 and A2 under stirring with a turbine. Afterwards the resulting mixture was left to cool to 50° C.

In a separate vessel, phase C was prepared: the compound Ac-L-Tyr-L-Glu-L-Lys-L-Leu-L-Gln-L-Val-NH$_2$ (Ac-SEQ ID NO:22-NH$_2$) previously dissolved in water [INCI: WATER (AQUA)], butylene glycol [INCI: BUTYLENE GLYCOL] and Silicone DC 200 [INCI: DIMETHICONE]. It was added slowly under stirring to phases A, A1, A2 and B. Afterwards Sepigel 305 [INCI: POLYACRYLAMIDE, WATER (AQUA), C13-14 ISOPARAFFIN, LAURETH-7] was added (phase D) stirring with a rotor until the mixture was homogenized. Afterwards the fragrance Tonus E20040401 (phase E) [INCI: FRAGRANCE (PARFUM)] was added, stirring with a rotor. The pH was adjusted to 6.0-6.5 with sodium hydroxide 20% [INCI: SODIUM HYDROXIDE, WATER (AQUA)] (phase F).

TABLE 15

Cosmetic composition containing Ac-SEQ ID NO: 22-$NH_2$

| Phase | Ingredients | % weight |
|---|---|---|
| A | WATER (AQUA) | 70.6300 |
| A | PENTYLENE GLYCOL | 5.0000 |
| A | GLYCERIN | 4.0000 |
| A | BENZYL ALCOHOL | 0.4000 |
| A1 | SCLEROTIUM GUM | 0.5000 |
| A2 | XANTHAN GUM | 0.3200 |
| B | GLYCERYL STEARATE | 2.5000 |
| B | CETEARYL ALCOHOL | 1.0000 |
| B | HYDROGENATED POLYISOBUTENE | 5.0000 |
| B | BISABOLOL | 2.0000 |
| B | SODIUM STEAROYL LACTYLATE | 1.5000 |
| B | POLYGLYCERYL-3 STEARATE | 1.5000 |
| B | PHENOXYETHANOL | 0.5000 |
| B | SHEA BUTTER (*BUTYROSPERMUM PARKII*) | 1.0000 |
| B | POLYSORBATE 20 | 0.5000 |
| C | Ac-SEQ ID NO: 22-$NH_2$ | 0.0010 |
| C | BUTYLENE GLYCOL | 1.6000 |
| C | WATER (AQUA) | 0.3990 |
| C | DIMETHICONE | 1.0000 |
| D | SEPIGEL 305 (POLYACRYLAMIDE, WATER (AQUA), C13-14 ISOPARAFFIN, LAURETH-7) | |
| | POLYACRYLAMIDE | 0.2000 |
| | WATER (AQUA) | 0.1700 |
| | C13-14 ISOPARAFFIN | 0.1000 |
| | LAURETH-7 | 0.0300 |
| E | FRAGRANCE (PARFUM) | 0.1500 |
| F | SODIUM HYDROXIDE 20% (SODIUM HYDROXIDE, WATER (AQUA) | q.s.p. pH 6.0-6.5 |

Example 19

Effect of the Composition of Example 18 on Repairing DNA Damage to the Skin Induced by UV Radiation A clinical study was carried out to assess the effectiveness of a cosmetic composition that contains Ac-SEQ ID NO:22-$NH_2$ on the repair to DNA damage of the skin induced by UV radiation. UV radiation, particularly the spectrum of UVB radiation present in sunlight, induces different types of DNA damage among which is the formation of cyclobutane pyrimidine dimers.

Twenty-one volunteers over the age of 18 participated in the study, both men and women, with healthy phototype II skin. From 4 weeks before beginning the study the volunteers could not apply topical medication to their arms or systematically administer themselves with corticosteroids and/or antihistamines. For the 2 weeks before the start of the study the volunteers could not administer anti-inflammatory products or antibiotics. From one week before the beginning of the study and throughout the duration of the study the application of bath and/or shower oils and skincare products to their arms was prohibited.

Four places on the underside of the volunteers' forearms were selected, and three of them were irradiated with a dose of UV equivalent to double the minimum dose that causes erythema (MED), previously determined for each volunteer. Immediately afterwards the volunteers topically applied the cream from Example 18 to themselves on one of the irradiated places and to another irradiated place they applied a placebo cream, with the same composition as the cream from Example 18 but without compound Ac-SEQ ID NO:22-$NH_2$ which was replaced with water in its percentage in the placebo composition. After 6 hours suction biopsies were taken from each of the irradiated areas, the application of the creams to their respective areas was repeated and the sampling from each of the irradiated areas 24 hours after irradiation was repeated. As a negative control samples were taken from the untreated non-irradiated place on the forearm, as a positive control a sample was taken from the untreated irradiated place on the forearm.

The quantity of cyclobutane pyrimidine dimers formed on the skin by UV radiation was determined by immunohistochemical analysis of the samples extracted, detecting the dimers by the ELISA technique and subsequently analyzing the images obtained in a microscope to determine the dimer accumulation factor (CPD score) on the epidermal cell nuclei.

TABLE 16

Repair effect of DNA damaged by UV radiation

| Treatment | CPD score | |
|---|---|---|
| | T 6 h | T 24 h |
| Control (Irradiated + untreated) | 155.4 | 97.5 |
| Irradiated + placebo composition | 144.8 | 93.7 |
| Irradiated + composition with Ac-SEQ ID NO: 22-$NH_2$ | 134.1 | 81.3 |

The composition that contained Ac-SEQ ID NO:22-$NH_2$ induced a lower accumulation of DNA damage of the skin after UV irradiation than the placebo composition.

Example 20

Study of the Profile of the Gene Expression of Human Epidermal Keratinocytes

The number of times that sets of genes corresponding to different biological functions significantly increase was studied, within the gene profile of human epidermal keratinocytes, with regard to the basal levels in untreated cells (negative control) by treatment with 0.1 mg/ml of the compound Ac-L-Tyr-L-Glu-L-Lys-L-Leu-L-Gln-L-Val-$NH_2$ (Ac-SEQ ID NO:22-$NH_2$). Adult human epidermal keratinocytes (HEKa) were seeded ($15 \times 10^4$ cells/vial cells/vial T25 $cm^2$), and were incubated in complete Epilife medium for 7 days at 37° C. in an atmosphere with 5% $CO_2$. After the incubation, the cells were treated for 24 hours at 37° C. in an atmosphere with 5% $CO_2$ with 0.1 mg/ml of the compound Ac-L-Tyr-L-Glu-L-Lys-L-Leu-L-Gln-L-Val-$NH_2$ (Ac-SEQ ID NO:22-$NH_2$) in complete Epilife medium or in complete Epilife medium as a negative control. The incubations and the treatments were carried out in duplicate for each condition.

24 hours after the treatments, the cells were homogenized and the RNA was extracted and purified from each replica and each condition by means of the RNeasyPlus Mini kit by Qiagen. Briefly, RNases were inactivated from cells lysates and samples were passed through special RNA binding columns to eliminate contaminants and impurities and after several microcentrifugation washes, the purified RNA was eluted with 50 µl of ultrapure water. The purity, integrity and concentration of the RNA obtained was evaluated by means of spectrophotometry (Nanodrop) and with a bioanalyzer (Agilent Bioanalyzer).

The marking of the purified RNA was carried out as was the hybridization of the samples in a human gene expression microarray (ASurePrint G3, Agilent). The normalized values obtained with the treatment were compared with the normalized values obtained with the negative control to obtain genes with differential expression. Next, a parametric analysis of the data was carried out by means of the Bioconductor software. Then, the values obtained were evaluated by means of GSEA (Gene Set Analysis Enrichment) to group the genes with differential expression in terms of Gene Ontology. Biological Routes and most significant pathways with a False Discovery Rate (FDR) lower than 25% were selected.

The results obtained are shown below in different tables in which different families of genes are grouped together.

TABLE 17

DNA REPAIR
Genes of the Protein DNA Complex Assembly overexpressed by the compound Ac-SEQ ID NO: 22-NH$_2$

| Symbol | Name | % Expression induction |
|---|---|---|
| TAF5 | TAF5 RNA polymerase II, TATA box binding protein (TBP)-associated factor, 100 kDa | 8.18 |
| ERCC8 | excision repair cross-complementing rodent repair deficiency, complementation group 8 | 8.90 |
| CDK7 | cyclin-dependent kinase 7 | 14.31 |
| MNAT1 | menage a trois homolog 1, cyclin H assembly factor (*Xenopus laevis*) | 17.84 |
| TAF2 | TAF2 RNA polymerase II, TATA box binding protein (TBP)-associated factor, 150 kDa | 25.12 |
| MED4 | mediator complex subunit 4 | 28.80 |
| MED14 | mediator complex subunit 14 | 32.54 |
| MED17 | mediator complex subunit 17 | 46.25 |
| MED13 | mediator complex subunit 13 | 56.75 |
| TAF1 | TAF1 RNA polymerase II, TATA box binding protein (TBP)-associated factor, 250 kDa | 65.00 |

TABLE 18

Genes involved in CELL CYCLE overexpressed by the compound Ac-SEQ ID NO: 22-NH$_2$

| Symbol | Name | % Expression induction |
|---|---|---|
| RAD17 | RAD17 homolog (*S. pombe*) | 0.21 |
| RAD21 | RAD21 homolog (*S. pombe*) | 18.22 |
| XRCC2 | X-ray repair complementing defective repair in Chinese hamster cells 2 | 24.95 |
| RAD54B | RAD54 homolog B (*S. cerevisiae*) | 26.20 |
| MSH4 | mutS homolog 4 (*E. coli*) | 33.28 |
| RAD50 | RAD50 homolog (*S. cerevisiae*) | 37.66 |
| ATM | ataxia telangiectasia mutated | 48.53 |

TABLE 19

Genes involved in HELICASE ACTIVITY and ATPase ACTIVITY overexpressed by the compound Ac-SEQ ID NO: 22-NH$_2$

| Symbol | Name | % Expression induction |
|---|---|---|
| DDX25 | DEAD (Asp-Glu-Ala-Asp) box helicase 25 | 16.24 |

TABLE 19-continued

Genes involved in HELICASE ACTIVITY and ATPase ACTIVITY overexpressed by the compound Ac-SEQ ID NO: 22-NH$_2$

| Symbol | Name | % Expression induction |
|---|---|---|
| DDX1 | DEAD (Asp-Glu-Ala-Asp) box helicase 1 | 26.92 |
| DDX10 | DEAD (Asp-Glu-Ala-Asp) box polypeptide 10 | 27.49 |
| SMARCA1 | SWI/SNF related, matrix associated, actin dependent regulator of chromatin, subfamily a, member 1 | 29.62 |
| WRN | Werner syndrome, RecQ helicase-like | 35.25 |
| CHD1 | chromodomain helicase DNA binding protein 1 | 40.46 |
| CHD2 | chromodomain helicase DNA binding protein 2 | 42.59 |
| ATRX | alpha thalassemia/mental retardation syndrome X-linked | 48.65 |
| SETX | senataxin | 65.33 |
| ERCC6 | excision repair cross-complementing rodent repair deficiency, complementation group 6 | 74.50 |

TABLE 20

Genes involved in DNA POLYMERASE ACTIVITY overexpressed by the compound Ac-SEQ ID NO: 22-NH$_2$

| Symbol | Name | % Expression induction |
|---|---|---|
| POLH | polymerase (DNA directed), eta | 28.96 |
| POLA1 | polymerase (DNA directed), alpha 1, catalytic subunit | 29.28 |
| POLD4 | polymerase (DNA-directed), delta 4 | 31.74 |
| PAPD7 | PAP associated domain containing 7 | 65.27 |

TABLE 21

LONGEVITY
Genes involved in TELOMERE MAINTENANCE AND PROTECTION overexpressed by the compound Ac-SEQ ID NO: 22-NH$_2$

| Symbol | Name | % Expression induction |
|---|---|---|
| TERF1 | telomeric repeat binding factor (NIMA-interacting) 1 | 7.38 |
| ACD | adrenocortical dysplasia homolog (mouse) | 10.76 |
| TINF2 | TERF1 (TRF1)-interacting nuclear factor 2 | 13.37 |
| TERF2IP | telomeric repeat binding factor 2, interacting protein | 21.63 |
| TEP1 | telomerase-associated protein 1 | 38.49 |

TABLE 22

Other genes involved in LONGEVITY overexpressed by the compound Ac-SEQ ID NO: 22-NH$_2$

| Symbol | Name | % Expression induction |
|---|---|---|
| PTEN | phosphatase and tensin homolog | 26.04 |

TABLE 23

APOPTOSIS
Genes involved in APOPTOSIS ACTIVATION differentially
expressed by the compound Ac-SEQ ID NO: 22-NH$_2$

| Symbol | Name | % Expression induction |
|---|---|---|
| MCL1 | myeloid cell leukemia sequence 1 (BCL2-related) | −17.76 |
| TP53BP2 | tumor protein p53 binding protein, 2 | 22.34 |
| CASP3 | caspase 3, apoptosis-related cysteine peptidase | 31.18 |
| MYC | v-myc myelocytomatosis viral oncogene homolog (avian) | 41.70 |
| SH3GLB1 | SH3-domain GRB2-like endophilin B1 | 52.57 |

TABLE 24

Genes involved in APOPTOSIS INHIBITION differentially
expressed by the compound Ac-SEQ ID NO: 22-NH$_2$

| Symbol | Name | % Expression induction |
|---|---|---|
| BAX | BCL2-associated X protein | −60.73 |
| MAPK8 | mitogen-activated protein kinase 8 | −33.72 |
| FAS | Fas (TNF receptor superfamily, member 6) | −15.36 |
| BIRC3 | baculoviral IAP repeat containing 3 | 16.84 |
| TAX1BP1 | Tax1 (human T-cell leukemia virus type I) binding protein 1 | 19.23 |
| BNIP2 | BCL2/adenovirus E1B 19 kDa interacting protein 2 | 30.68 |
| BNIP3L | BCL2/adenovirus E1B 19 kDa interacting protein 3-like | 31.39 |
| BAG4 | BCL2-associated athanogene 4 | 32.42 |
| BCL2L2 | BCL2-like 2 | 32.49 |
| XIAP | X-linked inhibitor of apoptosis | 51.98 |
| BCL2 | B-cell CLL/lymphoma 2 | 59.91 |
| BIRC6 | baculoviral IAP repeat containing 6 | 73.14 |

TABLE 25

INFLAMMATION
Genes involved in ANTI-INFLAMMATORY RESPONSE differentially
expressed by the compound Ac-SEQ ID NO: 22-NH$_2$

| Symbol | Name | % Expression induction |
|---|---|---|
| IL6 | interleukin 6 (interferon, beta 2) | −26.30 |
| ANXA1 | annexin A1 | 8.22 |
| ANXA4 | annexin A4 | 17.69 |
| AIF1 | allograft inflammatory factor 1 | 19.02 |
| ANXA5 | annexin A5 | 22.32 |
| NLRP3 | NLR family, pyrin domain containing 3 | 36.49 |
| NLRP12 | NLR family, pyrin domain containing 12 | 39.96 |
| SOCS2 | suppressor of cytokine signaling 2 | 56.13 |

The invention claimed is:

1. A compound consisting of general formula (I):

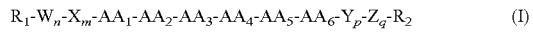  (I)

its stereoisomers, mixtures thereof and/or its cosmetically or pharmaceutically acceptable salts, wherein $AA_1$ is -Tyr-;

$AA_2$ is selected from the group consisting of -Asn-, -His-, -Tyr- and -Glu-;

$AA_3$ is selected from the group consisting of -Lys-, -Ser- and -Pro-;

$AA_4$ is selected from the group consisting of -Gly-, -Leu-, -Lys- and -His-;

$AA_5$ is selected from the group consisting of -Gln- and -Asn-;

$AA_6$ is -Val-;

W, X, Y, Z are independently selected amino acids;

n, m, p and q are independently selected and have a value of 0 or 1;

n+m+p+q is smaller than or equal to 2;

$R_1$ is selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic groups, substituted or unsubstituted alicyclyl, substituted or unsubstituted aryl, substituted or unsubstituted aralkyl, substituted or unsubstituted heterocyclyl, and substituted or unsubstituted heteroarylalkyl;

$R_2$ is selected from the group consisting of —$NR_3R_4$, —$OR_3$ and —$SR_3$, wherein $R_3$ and $R_4$ are independently selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ and $R_2$ are not α-amino acids.

2. The compound according to claim 1 wherein $AA_5$ is -Gln-.

3. The compound according to claim 1 wherein $R_1$ is selected from the group consisting of H, acetyl, lauroyl, myristoyl and palmitoyl, $AA_1$ is -L-Tyr-, $AA_2$ is -L-Asn-, $AA_3$ is -L-Lys-, $AA_4$ is -Gly-, $AA_5$ is -L-Gln-, $AA_6$ is -L-Val- and $R_2$ is selected from the group consisting of —$NR_3R_4$ and —$OR_3$ wherein $R_3$ and $R_4$ are independently selected from H, methyl, ethyl, hexyl, dodecyl and hexadecyl.

4. The compound according to claim 1 wherein $R_1$ is selected from the group consisting of H, acetyl, lauroyl, myristoyl and palmitoyl, $AA_1$ is -L-Tyr-, $AA_2$ is -L-Glu-, $AA_3$ is -L-Lys-, $AA_4$ is -L-Leu-, $AA_5$ is -L-Gln-, $AA_6$ is -L-Val- and $R_2$ is selected from the group consisting of -$NR_3R_4$ and -$OR_3$, wherein $R_3$ and $R_4$ are independently selected from H, methyl, ethyl, hexyl, dodecyl and hexadecyl.

5. The compound according to claim 1 wherein $R_1$ is selected from the group consisting of H, acetyl, lauroyl, myristoyl and palmitoyl, $AA_1$ is -L-Tyr-, $AA_2$ is -L-Glu-, $AA_3$ is -L-Ser-, $AA_4$ is -L-Lys-, $AA_5$ is -L-Gln-, $AA_6$ is -L-Val- and $R_2$ is selected from the group consisting of —$NR_3R_4$ and —$OR_3$, wherein $R_3$ and $R_4$ are independently selected from H, methyl, ethyl, hexyl, dodecyl and hexadecyl.

6. A cosmetic or pharmaceutical composition which comprises at least one compound of general formula (I), its stereoisomers, mixtures thereof and/or its cosmetically or pharmaceutically acceptable salts, according to claim 1 together with at least one cosmetically or pharmaceutically acceptable excipient or adjuvant.

7. The composition according to claim 6, wherein said compound of general formula (I), its stereoisomers, mixtures thereof and/or its cosmetically or pharmaceutically acceptable salts, is incorporated into a cosmetically or pharmaceutically acceptable delivery system or sustained release system selected from the group consisting of liposomes, mixed liposomes, oleosomes, niosomes, ethosomes, milliparticles, microparticles, nanoparticles, solid lipid nanoparticles, nanostructured lipid carriers, sponges, cyclodextrins, vesicles, micelles, mixed micelles of surfactants, surfactant-phospholipid mixed micelles, millispheres, microspheres, nanospheres, lipospheres, millicapsules, microcapsules, nanocapsules, microemulsions and nanoemulsions or is absorbed onto a solid organic polymer or solid mineral support selected from the group consisting of talc, bentonite, silica, starch and maltodextrin.

8. The composition according to claim 6, wherein said composition is present in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils, sprays, aerosols, capsules, gelatin capsules, soft capsules, hard capsules, tablets, sugar coated tablets, tablets, pills, powders, granules, chewing gum, solutions, suspensions, emulsions, syrups, elixirs, jellies and gelatins.

9. The composition according to claim 6 wherein said composition also comprises at least one cosmetically or pharmaceutically acceptable ingredient selected from the group consisting of DNA protection agents, DNA repair agents, stem cell protecting agents, agents inhibiting neuronal exocytosis, anticholinergic agents, agents inhibiting muscular contraction, antiaging agents, anti-wrinkle agents, antiperspirant agents, anti-inflammatory and/or analgesic agents, anti-itching agents, calming agents, anesthetic agents, inhibitors of acetylcholine-receptor aggregation, inhibitors of acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, detoxifying agents, antihistamine agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, hydrolytic epidermal enzymes, vitamins, amino acids, proteins, pigments, colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulation agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, AQP-3 modulating agents, aquaporin synthesis-stimulating agents, proteins of the aquaporin family, hyaluronic acid synthesis-stimulating agents, glycosaminoglycan synthesis-stimulating agents, fibronectin synthesis-stimulating agents, sirtuin synthesis-stimulating agents, sirtuin-activating agents, heat shock proteins, heat shock protein synthesis-stimulating agents, agents stimulating the synthesis of lipids and components of the stratum corneum, ceramides, fatty acids, agents that inhibit collagen degradation, agents that inhibit matrix metalloproteinase, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, antihyperkeratosis agents, comedolytic agents, anti-psoriatic agents, stabilizers, agents for the treatment and/or care of sensitive skin, firming agents, anti-stretch mark agents, binding agents, agents regulating sebum production, lipolytic agents or agents stimulating lipolysis, adipogenic agents, agents modulating PGC-1 αexpression, agents modulating the activity of PPARy, agents which increase or reduce the triglyceride content of adipocytes, anti-cellulite agents, agents which inhibit PAR-2 activity, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, agents delaying hair loss, preservatives, perfumes, cosmetic and/or absorbent and/or body odor-masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, and mixtures thereof.

10. The composition according to claim 9, where the cosmetically or pharmaceutically acceptable ingredient is acetyl tetrapeptide-40 or saccharide isomerate.

11. The cosmetic or pharmaceutical composition according to claim 6, wherein the compound is from 0.00000001% to 20% of the total weight of the composition.

12. The cosmetic or pharmaceutical composition according to claim 11, wherein the compound is from 0.000001% to 15% of the total weight of the composition.

13. The composition of claim 6, wherein $R_1$ is not H and $R_2$ is not OH.

14. composition of claim 6, wherein n+m+p+q is smaller than or equal to 1.

15. A compound consisting of general formula (I):

$$R_1\text{-}W_n\text{-}X_m\text{-}AA_1\text{-}AA_2\text{-}AA_3\text{-}AA_4\text{-}AA_5\text{-}AA_6\text{-}Y_p\text{-}Z_q\text{-}R_2 \qquad (I)$$

its stereoisomers, mixtures thereof and/or its cosmetically or pharmaceutically acceptable salts, wherein
$AA_1$ is -Tyr-;
$AA_2$ is selected from the group consisting of -Asn-, -His-, -Tyr- and -Glu-;
$AA_3$ is selected from the group consisting of -Lys-, -Ser- and -Pro-;
$AA_4$ is selected from the group consisting of -Gly-, -Leu-, -Lys- and -His-;
$AA_5$ is selected from the group consisting of -Gln- and -Asn-;
$AA_6$ is -Val-;
W, X, Y, Z are independently selected amino acids;
n, m, p and q are independently selected and have a value of 0 or 1;
n+m+p+q is smaller than or equal to 2;
$R_1$ is selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic groups, substituted or unsubstituted alicyclyl, substituted or unsubstituted aryl, substituted or unsubstituted aralkyl, substituted or unsubstituted heterocyclyl, and substituted or unsubstituted heteroarylalkyl;
$R_2$ is selected from the group consisting of —$NR_3R_4$, —$OR_3$ and —$SR_3$, wherein $R_3$ and $R_4$ are independently selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, and substituted or unsubstituted aralkyl;
$R_1$ and $R_2$ are not a-amino acids; and
at least one of:
$R_1$ is not H, and
$R_2$ is not OH.

16. A method for cosmetic, non-therapeutic treatment and/or care of the skin, hair and/or mucous membranes comprising administering the compound of general formula (I), its stereoisomers, mixtures thereof and/or its cosmetically or pharmaceutically acceptable salts, according to claim 1 to the skin, hair and/or mucous membranes.

17. The method according to claim 16, wherein the treatment is for treating aging and/or photoaging of the skin, hair and/or mucous membranes.

18. A method for delay of cell senescence and/or in the increase of cell longevity comprising administering the compound of general formula (I), its stereoisomers, mixtures thereof and/or its cosmetically or pharmaceutically acceptable salts, according to claim 1 to a body of a mammal.

19. A method for repair of damaged DNA comprising administering the compound of general formula (I), its stereoisomers, mixtures thereof and/or its cosmetically or pharmaceutically acceptable salts, according to claim 1 to a body of a mammal.

20. A method for stimulation of the expression of proteins regulated by forkhead transcription factors, subclass O (FOXO) comprising administering the compound of general formula (I), its stereoisomers, mixtures thereof and/or its cosmetically or pharmaceutically acceptable salts, according to claim 1 to a body of a mammal.

21. A method for regulation of cell apoptosis comprising administering the compound of general formula (I), its stereoisomers, mixtures thereof and/or its cosmetically or pharmaceutically acceptable salts, according to claim 1 to a body of a mammal for the regulation of cell apoptosis.

SEQUENCE LISTING

```
<160> NUMBER OF SEQ ID NOS: 45

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Tyr Asn Lys Gly Gln Val
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Tyr Tyr Ser Leu Asn Val
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Tyr Glu Pro Lys Gln Val
1               5
```

```
<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Tyr Asn Lys His Gln Val
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Tyr Asn Lys Gly Asn Val
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Tyr Tyr Ser Gly Gln Val
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Tyr Glu Pro Leu Asn Val
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Tyr Asn Lys Lys Gln Val
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Tyr Tyr Ser His Asn Val
1               5
```

```
<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Tyr Glu Pro Gly Gln Val
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Tyr Asn Lys Leu Asn Val
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Tyr Tyr Ser Lys Gln Val
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Tyr Glu Pro His Asn Val
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Tyr Glu Ser Lys Asn Val
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Tyr Tyr Pro Gly Asn Val
1               5
```

```
<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Tyr Glu Ser Gly Gln Val
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

Tyr Asn Pro Lys Asn Val
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Tyr Asn Pro His Gln Val
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Tyr Glu Ser His Gln Val
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Tyr Tyr Ser His Gln Val
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Tyr Asn Lys Leu Gln Val
1               5

<210> SEQ ID NO 22
```

```
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Tyr Glu Lys Leu Gln Val
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Tyr Tyr Lys Leu Gln Val
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Tyr Glu Ser Lys Gln Val
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Tyr His Lys Leu Gln Val
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Tyr His Ser Lys Gln Val
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide

<400> SEQUENCE: 27

Tyr Asn Ser Lys Gln Val
1               5

<210> SEQ ID NO 28
<211> LENGTH: 6
```

```
<212> TYPE: PRT
<213> ORGANISM: Artificial Sequence
<220> FEATURE:
<223> OTHER INFORMATION: Synthetic peptide

<400> SEQUENCE: 28

Tyr His Pro His Gln Val
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29

Tyr Tyr Pro His Gln Val
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide

<400> SEQUENCE: 30

Tyr His Ser His Gln Val
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Tyr Asn Lys Leu Gln Val Gly
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Tyr Glu Lys Leu Gln Val Ala
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Leu Tyr Tyr Lys Leu Gln Val
1               5

<210> SEQ ID NO 34
<211> LENGTH: 7
<212> TYPE: PRT
```

<213> ORGANISM: Artificial Sequence
<220> FEATURE:
<223> OTHER INFORMATION: Synthetic peptide

<400> SEQUENCE: 34

Ala Tyr Glu Ser Lys Gln Val
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic peptide

<400> SEQUENCE: 35

Gly Leu Tyr Asn Lys Gly Gln Val
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Ala Tyr Asn Pro His Gln Val Gly
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic peptide

<400> SEQUENCE: 37

Asn Glu Tyr Glu Ser His Gln Val
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic peptide

<400> SEQUENCE: 38

Ala Tyr Tyr Ser His Gln Val Leu
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide

<400> SEQUENCE: 39

Tyr Asn Pro His Asn Val
1               5

<210> SEQ ID NO 40
<211> LENGTH: 6
<212> TYPE: PRT
<213> ORGANISM: Artificial Sequence

```
<220> FEATURE:
<223> OTHER INFORMATION: Synthetic peptide

<400> SEQUENCE: 40

Tyr Glu Pro His Gln Val
1               5

<210> SEQ ID NO 41
<211> LENGTH: 6
<212> TYPE: PRT
<213> ORGANISM: Artificial Sequence
<220> FEATURE:
<223> OTHER INFORMATION: Synhetic peptide

<400> SEQUENCE: 41

Tyr Asn Ser His Gln Val
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide

<400> SEQUENCE: 42

Tyr Tyr Pro Lys Gln Val
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic peptide

<400> SEQUENCE: 43

Tyr Tyr Pro Lys Asn Val
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide

<400> SEQUENCE: 44

Tyr Glu Lys Leu Asn Val
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide

<400> SEQUENCE: 45

Tyr Tyr Lys Leu Asn Val
1               5
```